US008916200B2

(12) United States Patent
Singh et al.

(10) Patent No.: US 8,916,200 B2
(45) Date of Patent: Dec. 23, 2014

(54) NANOIMPRINT LITHOGRAPHY FORMATION OF FUNCTIONAL NANOPARTICLES USING DUAL RELEASE LAYERS

(75) Inventors: Vikramjit Singh, Austin, TX (US); Frank Y. Xu, Round Rock, TX (US); Sidlgata V. Sreenivasan, Austin, TX (US)

(73) Assignee: Molecular Imprints, Inc., Austin, TX (US)

( * ) Notice: Subject to any disclaimer, the term of this patent is extended or adjusted under 35 U.S.C. 154(b) by 217 days.

(21) Appl. No.: 13/289,601

(22) Filed: Nov. 4, 2011

(65) Prior Publication Data
US 2012/0114559 A1 May 10, 2012

Related U.S. Application Data

(60) Provisional application No. 61/410,632, filed on Nov. 5, 2010.

(51) Int. Cl.
*A61K 9/14* (2006.01)
*A61K 9/51* (2006.01)
*B82Y 5/00* (2011.01)
*G03F 7/00* (2006.01)
*B82Y 15/00* (2011.01)

(52) U.S. Cl.
CPC .............. *G03F 7/0002* (2013.01); *B82Y 5/00* (2013.01); *A61K 9/51* (2013.01); *A61K 9/5192* (2013.01); *B82Y 15/00* (2013.01); *Y10S 977/701* (2013.01); *Y10S 977/712* (2013.01); *Y10S 977/713* (2013.01)
USPC ........... 424/489; 977/701; 977/712; 977/713; 424/9.1

(58) Field of Classification Search
CPC ......... A61K 9/14; A61K 9/51; A61K 9/5192; A61K 9/5107; A61K 9/5115; A61K 9/5123; B82Y 40/00; B82Y 30/00
USPC ......... 424/9.01, 489–499; 977/701, 712, 713, 977/773, 902, 904, 927
See application file for complete search history.

(56) References Cited

U.S. PATENT DOCUMENTS

| | | | |
|---|---|---|---|
| 6,696,220 B2 | 2/2004 | Bailey et al. | |
| 6,873,087 B1 | 3/2005 | Choi et al. | |
| 6,918,946 B2 | 7/2005 | Korgel et al. | |
| 6,936,194 B2 | 8/2005 | Watts | |
| 7,157,036 B2 | 1/2007 | Choi et al. | |
| 7,179,396 B2 | 2/2007 | Sreenivasan | |
| 7,396,475 B2 | 7/2008 | Sreenivasan | |
| 7,635,263 B2 | 12/2009 | Cherala et al. | |
| 7,635,445 B2 | 12/2009 | Choi et al. | |
| 7,636,999 B2 | 12/2009 | Choi et al. | |
| 7,705,237 B2 | 4/2010 | Swanson | |
| 7,759,407 B2 | 7/2010 | Xu | |
| 7,798,801 B2 | 9/2010 | Babbs et al. | |
| 2004/0065252 A1 | 4/2004 | Sreenivasan et al. | |
| 2004/0065976 A1 | 4/2004 | Sreenivasan et al. | |
| 2004/0178076 A1 | 9/2004 | Stonas et al. | |
| 2004/0241896 A1 | 12/2004 | Zhou et al. | |
| 2005/0187339 A1 | 8/2005 | Xu et al. | |
| 2005/0276743 A1 * | 12/2005 | Lacombe et al. | ........... 423/447.3 |
| 2006/0014001 A1 * | 1/2006 | Zhang et al. | ............... 428/195.1 |
| 2006/0021967 A1 | 2/2006 | Lee | |
| 2006/0063387 A1 | 3/2006 | Miller et al. | |
| 2006/0172031 A1 | 8/2006 | Babbs et al. | |
| 2007/0031505 A1 | 2/2007 | Roy et al. | |
| 2008/0122106 A1 | 5/2008 | Nitta et al. | |
| 2008/0182070 A1 | 7/2008 | Chou et al. | |
| 2009/0061152 A1 | 3/2009 | DeSimone et al. | |
| 2009/0196826 A1 | 8/2009 | Gao et al. | |
| 2010/0120251 A1 | 5/2010 | Sreenivasan et al. | |
| 2011/0049096 A1 | 3/2011 | Sreenivasan et al. | |
| 2011/0190463 A1 | 8/2011 | Xu et al. | |

FOREIGN PATENT DOCUMENTS

| | | |
|---|---|---|
| EP | 2216680 A2 | 8/2010 |
| EP | 2312393 | 4/2011 |
| GB | 2334347 | 8/1999 |
| WO | WO/02/29136 | 4/2002 |
| WO | WO/2007/081410 | 7/2007 |
| WO | WO/2007/094829 | 8/2007 |
| WO | WO/2008/106503 | 9/2008 |
| WO | WO/2009/014848 | 1/2009 |
| WO | WO2011094672 | 8/2011 |

OTHER PUBLICATIONS

Supplementary European Search Report for EP11838904, dated May 9, 2014.

Jang et al. Nanoscopic Pd Line Arrays Using Nanocontact Printed Dendrimers; Langmuir Mar. 28, 2006 American Chemical Society vol. 22 No. 7, pp. 3326-3331 (Mar. 28, 2006).

Hu et al., High-Moment Antiferromagnetic Nanoparticles with Tunable Magnetic Properties, Advanced Materials 2008, vol. 20 pp. 1479-1483.

(Continued)

*Primary Examiner* — Michael G Hartley
*Assistant Examiner* — Micah-Paul Young
(74) *Attorney, Agent, or Firm* — Cameron A. King

(57) ABSTRACT

Functional nanoparticles may be formed using at least one nanoimprint lithography step. In one embodiment, sacrificial material may be patterned on a multilayer substrate including one or more functional layers between removable layers using an imprint lithography process. At least one of the functional layers includes a functional material such as a pharmaceutical composition or imaging agent. The pattern may be further etched into the multilayer substrate. At least a portion of the functional material may then be removed to provide a crown surface exposing pillars. Removing the removable layers releases the pillars from the patterned structure to form functional nanoparticles such as drug or imaging agent carriers.

17 Claims, 17 Drawing Sheets

(56) References Cited

OTHER PUBLICATIONS

Glanhchai et al., Nanoimprint lithography based fabrication of shape-specific, enzymatically-triggered smart nanoparticles, Journal of Controlled Release, 2008, vol. 125, pp. 283-272.

Gratton et al. Nanofabricated particles for engineered drug therapies: a preliminary biodistribution study of PRINT nanoparticles, J Control Release, Aug. 16, 2007; vol. 121, pp. 10-18.

Kelly et al., Shape-specific monodisperse nano-molding of protein particles; J. Am. Chem. Soc. 2008, vol. 130, pp. 5437-5439.

Canelas et al., Top-down particles fabrication: control of size and shape for diagnostic imaging and drug delivery; WIREs Nanomedicine and Nanobiotechnology, 2009, vol. 1, Jul. 1, 2009, pp. 391-404.

Hamidi et al., Hydrogel nanoparticles in drug delivery, Advanced Drug Delivery Reviews, vol. 60 (2008), pp. 1638-1649, Sep. 20, 2008.

Hans et al., Biodegradable nanoparticles for drug delivery and targeting; Current Opinion in Solid State and Materials Science, 2002. 6(4): p. 319-327, Sep. 4, 2002.

Hughes, Nanostructure-mediated drug delivery, Nanomedicine: nanotechnology, biology, and medicine, 2005. 1(1): p. 22-30. Nov. 30, 2004.

Brigger et al., Nanoparticles in cancer therapy and diagnosis, Advanced Drug Delivery Reviews, 2002. 54(5): p. 631-651. May 10, 2002.

Egitto, Plasma Etching and Modification of Organic Polymers; Pure and Applied Chemistry, 62:9 (1990) 1699-1708.

Kushida et al., Dry-Etching Durability of Copolymers and Polymer Blends of Vinylnaphthalene or α-Methylstyrene with Methyl Methacrylate; Japanese Journal of Applied Physics, 34:1:8A (1995) 4234-4238 May 31, 1995.

Cho et al., Identification of Hydrophilic Group Formation on Polymer Surface during Ar+ Ion Irradiation in O2 Environment; Material Research Society Symposium Proceedings 438 (1997) 517-532.

Koh et al., Surface Modification of Polymer by Ion Assisted Reaction in Reactive Gases Environment; Material Research Society Symposium Proceedings 438 (1997) 505-510.

Hollander et al., On Depth Profiling of Polymers by Argon Ion Sputtering; Plasma Processes and Polymers, 4 (2007) 773-776.

Qui et al., Design and Evaluation of Layered Diffusional Matrices for Zero-Order Sustained-Release; Journal of Controlled Release, vol. 51 (1998), pp. 123-130, May 30, 1997.

Qui et al., Design of a Core-Shelled Polymer Cylinder for Potential Programmable Drug Delivery; International Journal of Pharmaceutics, vol. 219, pp. 151-160, May 5, 2001.

Okuda et al., Time-programmed Dual Release Formulation by Multilayered Drug-loaded Nanofiber Meshes; Journal of Controlled Release, vol. 143, pp. 258-264, Jan. 13, 2010.

Akita et al., Multilayered Nanoparticles for Penetrating the Endosome and Nuclear Membrane via a Step-wise Membrane Fusion Process; Biomaterials, vol. 30 (2009), pp. 2940-2049, Mar. 4, 2009.

* cited by examiner

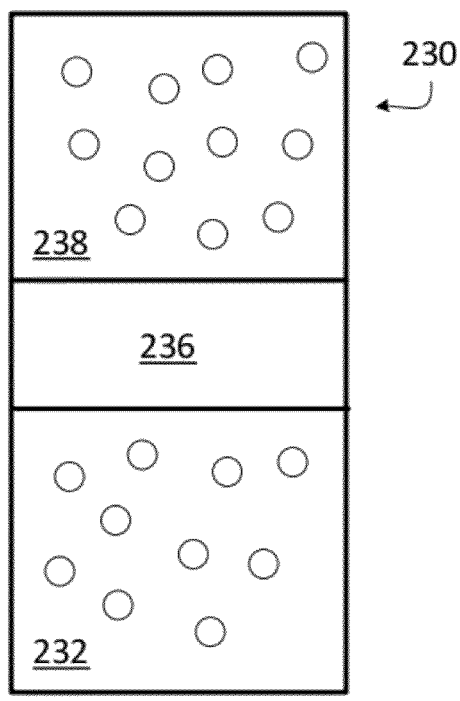
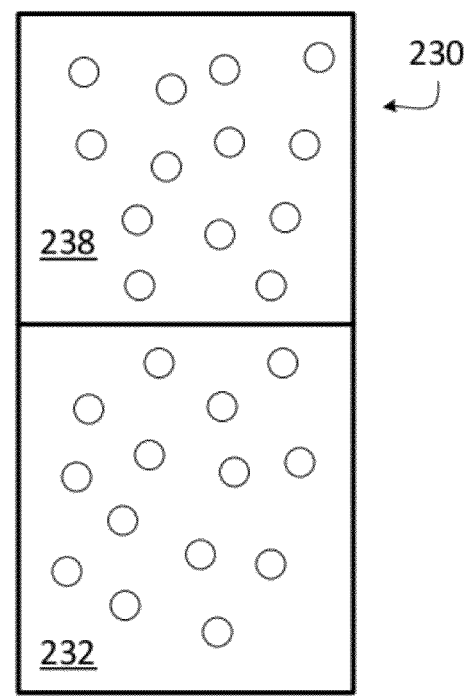
*FIG. 19A*  *FIG. 19B*

NANOIMPRINT LITHOGRAPHY FORMATION OF FUNCTIONAL NANOPARTICLES USING DUAL RELEASE LAYERS

CROSS REFERENCE TO RELATED APPLICATIONS

The present application claims priority to U.S. provisional application No. 61/410,632 filed Nov. 5, 2010, which is hereby incorporated by reference.

BACKGROUND INFORMATION

Nano-fabrication includes the fabrication of very small structures that have features on the order of 100 nanometers or smaller. Although well known within the integrated circuit industry, nano-fabrication techniques may be applied in the bio-domain, solar cells industry, battery industry and/or other industries. See, for example, U.S. Patent Publication No. 2007/0031505; U.S. Pat. Nos. 6,918,946; 7,705,237; Kelly et al., *Shape-specific monodisperse nano-molding of protein particles*, J. Am. Chem. Soc. 2008, vol. 130, pgs. 5437-5439; and Canelas et al., *Top-down particles fabrication: control of size and shape for diagnostic imaging and drug delivery*, WIREs Nanomedicine and Nanobiotechnology, 2009, vol. 1, pgs. 391-404.

Imprint lithography techniques include formation of a relief pattern in a formable layer positioned on a substrate. The substrate may be coupled to a motion stage to obtain a desired positioning to facilitate the patterning process. The patterning process may use a template spaced apart from the substrate and the formable liquid applied between the template and the substrate. The formable liquid is solidified to form features on the substrate conforming to the shape of the template that contacts the formable liquid. After solidification, the template is separated from the features and the substrate is subjected to additional processing to form functional nanoparticles (e.g., drug delivery devices, batteries, and the like).

BRIEF DESCRIPTION OF DRAWINGS

FIGS. 19A and 19B are schematic cross-sectional views of a nanoparticle drug carrier with oppositely charged species in different layers.

DETAILED DESCRIPTION

Figure 1:
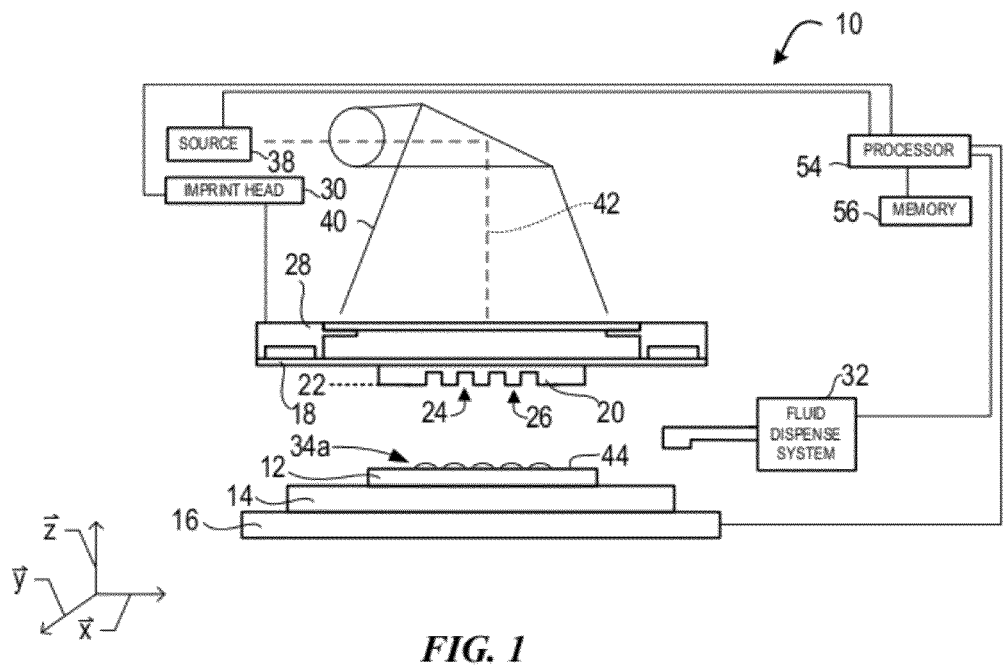
FIG. 1 illustrates a simplified side view of a lithographic system.
Figure 2:
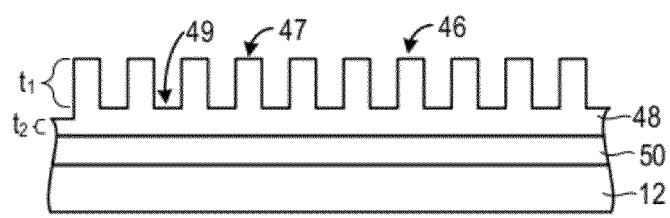
FIG. 2 illustrates a simplified side view of the substrate shown in FIG. 1 having a patterned layer positioned thereon.

Referring to the figures, and particularly to FIGS. 1 and 2, illustrated therein is a lithographic system 10 used to form functional nano- and/or microparticles on substrate 12. Substrate 12 may be coupled to substrate chuck 14. As illustrated, substrate chuck 14 is a vacuum chuck. Substrate chuck 14 however, may be any chuck including, but not limited to, vacuum, pin-type, groove-type, electrostatic, electromagnetic, and/or the like. Exemplary chucks are described in U.S. Pat. Nos. 6,873,087, 7,635,445, U.S. Patent Publication No. 2006-0172031, U.S. Pat. Nos. 7,636,999, and 7,635,263, all of which are hereby incorporated by reference herein in their entirety.

Substrate 12 and substrate chuck 14 may be further supported by stage 16. Stage 16 may provide rotational and/or translational motion in relation to the x, y and z axes. Stage 16, substrate 12, and substrate chuck 14 may also be positioned on a base (not shown).

Spaced-apart from substrate 12 is template 18. Template 18 may include mesa 20 extending therefrom towards substrate 12, with mesa 20 having a patterning surface 22 thereon. Further, mesa 20 may be referred to as mold 20. Alternatively, template 18 may be formed without mesa 20.

Template 18 and/or mold 20 may be formed from such materials including, but not limited to, fused-silica, quartz, silicon, organic polymers, siloxane polymers, borosilicate glass, fluorocarbon polymers, metal, hardened sapphire, and/or the like. As illustrated, patterning surface 22 comprises features defined by a plurality of spaced-apart recesses 24 and/or protrusions 26, though embodiments are not limited to such a configuration. For example, patterning surface 22 may be substantially flat. Generally, patterning surface 22 may be defined as any original pattern that forms the basis of a pattern to be formed on substrate 12. Additionally, template 18 may be treated with an anti-adhesion agent (e.g., RelMat®, available from Molecular Imprints, Inc., Austin, Tex. or (tridecafluoro-1,1,2,2-tetrahydrooctyl)trichlorosilane (FOTS)). Exemplary anti-adhesion agents include, but are not limited to those described in U.S. Pat. No. 6,696,220, which is hereby incorporated by reference herein in its entirety.

Template 18 may be coupled to chuck 28. Chuck 28 may be configured as, but not limited to, vacuum, pin-type, groove-type, electrostatic, electromagnetic, and/or other similar chuck types. Exemplary chucks are further described in U.S. Pat. No. 6,873,087, which is hereby incorporated by reference herein in its entirety. Further, chuck 28 may be coupled to imprint head 30 such that chuck 28 and/or imprint head 30 may be configured to facilitate movement of template 18.

Additionally, chuck 28 may be configured to adjust and/or vary the structure of template 18 prior to imprinting, during imprinting, and/or subsequent to imprinting (e.g. during separation).

System 10 may further include fluid dispense system 32. Fluid dispense system 32 may be used to deposit functional material 34a on substrate 12. Functional material 34a may include biocompatible materials (e.g., polyethylene glycol), pharmaceutical compositions with one or more active ingredients (e.g., one or more drugs), imaging agents, materials used in solar cells (e.g., n-type material, p-type material) or batteries, or other functional materials that demonstrate desirable properties in nanoparticle form.

Functional material 34a may be positioned on substrate 12 using techniques such as drop dispense, spin-coating, dip coating, spray coating, chemical vapor deposition (CVD), physical vapor deposition (PVD), thin film deposition, thick film deposition, and/or the like. It should be noted that the positioning of functional material 34 on substrate 12 may be configured to limit the amount of waste. For example, use of drop dispense in positioning of functional material 34 on substrate 12, as compared to spin-coating and the like, may limit the amount of non-useable fluid during formation of functional nanoparticles.

Substrate 12 may include a removable layer 50. Removable layer 50 may facilitate separation of solidified functional material 34a from substrate 12 as described herein. Examples of materials for use in removable layer 50 may include, but are not limited to PVA, PMMA, gelatin, and the like.

Referring to FIGS. 1 and 2, system 10 may further comprise solidification source 38 (e.g., energy source) coupled to direct a medium 40 (e.g., energy) along path 42 to solidify functional material 34a. Imprint head 30 and stage 16 may be configured to position template 18 and/or substrate 12 in superposition with path 42. System 10 may be regulated by processor 54 in communication with stage 16, imprint head 30, fluid dispense system 32 and/or source 38, and may operate on a computer readable program stored in memory 56.

Either imprint head 30, stage 16, or both may vary a distance between mold 20 and substrate 12 to define a desired volume therebetween that is filled by functional material 34a. For example, imprint head 30 may apply a force to template 18 such that mold 20 contacts functional material 34a. After the desired volume is filled with functional material 34a, source 38 may produce medium 40, e.g. UV radiation, causing functional material 34a to solidify and/or cross-link conforming to a shape of surface 44 of substrate 12 and patterning surface 22, defining patterned layer 46 on substrate 12. Patterned layer 46 may comprise a residual layer 48 and/or features (e.g., protrusions 47 and recessions 49). Protrusions 47 may have a thickness $t_1$ and residual layer 48 may have a thickness $t_2$.

Figure 3:
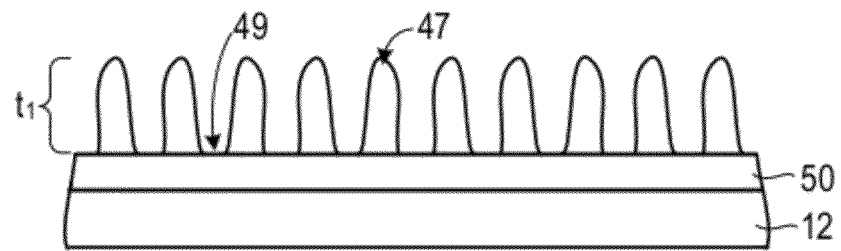
FIG. 3 illustrates a simplified side view of the substrate shown in FIG. 2 having multiple protrusions formed thereon.

Referring to FIGS. 2 and 3, after solidification, patterned layer 46 may be subjected to further processing to clean patterned layer 46 and/or further separate protrusions 47 to form pillars or nanoparticles 52. For example, patterned layer 46 may be subjected to an oxygen plasma etching. Etching may remove at least a portion (e.g., some or substantially all) of residual layer 48. FIG. 3 shows protrusions 47 on removable layer 50 after removal of substantially all of residual layer 48.

Figure 4:
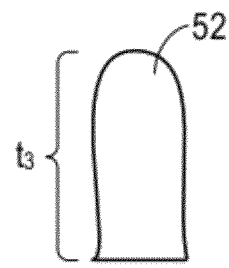
FIG. 4 illustrates a simplified side view of a pillar formed by release of the protrusions of FIG. 3.

Referring to FIGS. 3 and 4, release of protrusions 47 from substrate 12 may form pillars 52. For example, substrate 12 may be subjected to a solution that includes, but is not limited to, water (e.g., de-ionized water), organic solvents (e.g., DMSO), inorganic acids (e.g., dilute HF), basic solutions, and/or the like. The solution may release protrusions 47 from substrate 12 to form pillars 52 having a thickness $t_3$.

Etching of protrusion 47 subsequent to solidification of functional material 34a may distort the configuration of protrusion 47 such that thickness $t_2$ of protrusion 47 is substantially different from thickness $t_3$ of the resulting pillar 52. The amount of degradation of shape may limit the accuracy and/or precision of dimensionality when forming pillars 52. Such distortion may be disadvantageous depending on the design consideration for the pillar 52. For example, when pillars 52 are functional nanoparticles used as drug delivery devices (e.g., nanoparticle drug carriers), geo-targeting of destinations for pillar 52 within a body (e.g., human, animal, and/or the like) may be misdirected by alterations and/or distortion in shape.

Separation of template 18 from patterned layer 46 may also cause separation defects in pillars 52. Although release layers such as FOTS or RelMat®, and the like, may be provided on substrate 12, template 18, or both, the surface area of patterned layer 46 coupled to template 18 prior to separation may exceed the surface area of patterned layer 46 coupled to substrate 12. Materiality of release layers and/or functional material 34 in combination with the dynamics of the surface area may provide separation defects in pillars 52.

U.S. Patent Application Publication No. US 2011/0049096, incorporated herein by reference in its entirety, describes processes to minimize degradation and separation distortion in the formation of functional nanoparticles involving deposition of functional material within recessions formed in a removable layer. Functional nanoparticles formed through nanoimprint lithography processes described herein may include one or more different layers disposed between a first removable layer and a second removable layer. Nanoparticles including two or more pharmaceutical compositions in such a layered structure may be used for controlled release of multi-drugs selected to target specific regions of a subject. For example, multilayer nanoparticles including a combination of selected pharmaceutical compositions may be designed to provide a desired sequence or rate of release of active ingredients (e.g., in a controlled release manner), thereby enhancing treatment efficacy. The processes described herein provide for the formation of functional nanoparticles with controlled accuracy and precision and with minimized degradation and/or distortion. Such control extends both to the formation of the nanoparticles as a whole as well as to the formation of different layers that may make up the nanoparticles. For example, where nanoparticles are formed having at least two functional layers, the multilayer nanoparticle can be more accurately formed than in other processes, with the interfaces between adjacent layers being substantially planar. This allows for more precise control of the volume, and therefore the functional material (e.g., drug loading) of each layer of the nanoparticle, which in turn can provide more precise control of e.g. release kinetics.

Figure 5A:
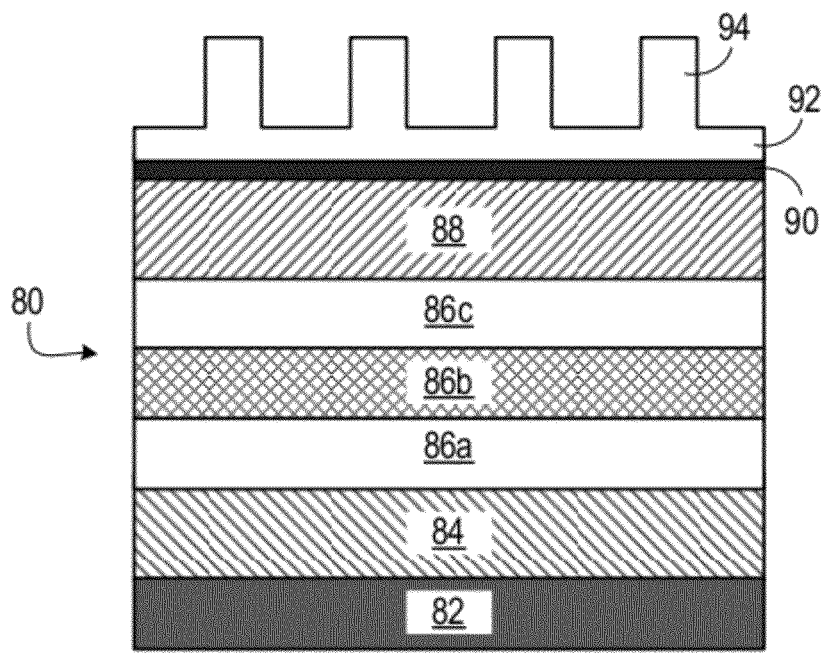
FIGS. 5A-5E illustrate simplified side views of formation of multilayer nanoparticles by imprint lithography.

FIGS. 5A-5E illustrate various stages in nanoimprint lithography processing of a multilayer substrate to form multilayer nanoparticles. Referring to FIG. 5A, multilayer substrate 80 includes base layer 82, removable layer 84, functional layers 86a, 86b, and 86c (formed from functional materials 86a', 86b', and 86c', respectively), removable layer 88, and optional adhesion layer 90.

Functional materials 86a', 86b', and 86c' may have uses within the bio-domain, the solar cell industry, the battery industry, and other areas in which functional nanoparticles are advantageous. For example, functional materials 86a', 86b', and 86c' may include, but are not limited to, one or more biocompatible polymers, solar cell materials, polymerizable materials, and the like. Solar cell materials include, for example, n-type material and p-type material. Biocompatible polymers include synthetic biocompatible polymers (including, e.g., poly(ethylene glycol) (PEG), poly(ethylene glycol) acrylate (PEGA), poly(ethylene glycol) diacrylate (PEGDA), poly(ethylene glycol) methacrylate (PEGMA), poly(ethylene glycol) dimethacrylate (PEGDMA), poly(lactic acid) (PLA), PLA-PEG copolymer, poly(glycolic acid) (PGA), poly(lactide-co-glycolide) copolymer (PLGA), PLGA-PEG copolymer, PEG-PLA-PEG, and P(NIPAAm-co-EMA) (copolymer of Poly(N-isopropyl acrylamide) and poly(ethyl methacrylate))), natural biocompatible polymers (including e.g., chitosan, dextran, dextran sulfate, agarose, polylysine, pectin, fibrin, carboxymethyl chitin, collagen, and gelatin), or any combination of synthetic and natural biocompatible polymers (including, e.g., chitosan-PEG, collagen-acrylate, alginate-acrylate, P(PEG-co-peptides), alginate-g-(PEO-PPO-PEO), and P(PLGA-co-serine). A biocompatible polymer or a mixture thereof can be used as a drug carrier solution for imprinting. Additional examples of biocompatible polymers include alginate (natural biocompatible polymer) and poly (vinyl alcohol), poly (ethylenoxide), poly (ethyleneimine), poly (vinyl pyrrolidone), and poly-N-isopropylacrylamide (synthetic biocompatible polymers). Other examples of biocompatible polymers are described in Hamidi et al., *Hydrogel nanoparticles in drug delivery*, Advanced Drug Delivery Reviews, vol. 60 (2008), pp. 1638-1649, Hans et al, *Biodegradable nanoparticles for drug delivery and targeting*, Current Opinion in Solid State and Materials Science, 2002. 6(4): p. 319-327, and Hughes, G. A., *Nanostructure-mediated drug delivery*, Nanomedicine: nanotechnology, biology, and medicine, 2005. 1(1): p. 22-30, each of which is hereby incorporated by reference herein in its entirety.

Representative drugs or pharmaceutical compositions or therapeutic agents that can be incorporated into functional materials that are comprised of such biocompatible polymers include, e.g., doxorubicin, isradipine, paclitaxel, estrogen, insulin, cisplatin, siRNA. Other examples of drugs, pharmaceutical compositions and therapeutic agents are described in Hamidi et al., *Hydrogel nanoparticles in drug delivery*, Advanced Drug Delivery Reviews, vol. 60 (2008), pp. 1638-1649, incorporated herein by reference in its entirety. Imaging agents can also be incorporated into the functional materials. Resultant functional nanoparticles can be used for diagnostic imaging purposes, including but not limited to fluorescent imaging and magnetic resonance imaging (MRI). Such imaging agents can include e.g. fluorescing molecules or superparamagnetic iron oxides (SPIOs). Examples of such imaging agents are described in Brigger et al., *Nanoparticles in cancer therapy and diagnosis*, Advanced Drug Delivery Reviews, 2002. 54(5): p. 631-651.

The multilayer substrate 80 may be formed as further described herein. Base layer 82 may be similar to substrate 12 described in relation to FIG. 1. Base layer 82 may be formed of materials including, but not limited to, fused-silica, quartz, silicon, organic polymers, siloxane polymers, borosilicate glass, fluorocarbon polymers, metal, hardened sapphire, and/or the like. Removable layer 84 may be positioned adjacent to base layer 82, and may have properties similar to those of removable layer 50 described in relation to FIG. 3. For example, removable layer 84 may dissolve when subjected to a solution including, but not limited to, water (e.g., de-ionized water), organic solvents (e.g., DMSO), inorganic acids (e.g., dilute HF), basic solutions, and/or the like.

As shown in FIG. 5A, multilayer substrate 80 includes three functional layers, however, a multilayer substrate may include any number of functional layers (e.g., one functional layer, two functional layers, four functional layers, five functional layers, etc.). Patterned layer 92, with features 94, may be formed of sacrificial material on removable layer 88 or adhesion layer 90, such sacrificial material for forming patterned layer 92 may be formed of materials including, but not limited to, a polymerizable fluid comprising a monomer mixture as described in U.S. Pat. No. 7,157,036 and/or U.S. Patent Publication No. 2005/0187339, both of which are hereby incorporated by reference herein in their entirety. Patterned layer 92 may be formed on multilayer substrate 80 using an imprint lithography template such as described in relation to the system 10 and processes described in FIGS. 1 and 2. It should be noted that patterned layer 92 may be formed by other nano-lithography techniques including, but not limited to, optical lithography, x-ray lithography, extreme ultraviolet lithography, scanning probe lithography, atomic force microscopic nanolithography, magneto lithography, and/or the like. Base layer 82 may be formed of materials such as fused-silica, quartz, silicon, organic polymers, siloxane polymers, borosilicate glass, fluorocarbon polymers, metal, hardened sapphire, or the like. In some cases, removable layer 84 may include a polymer such as, for example, poly(methyl methacrylate) (PMMA) or poly(vinyl alcohol) (PVA). Removable layer 84 may be applied to base layer 82 in a process including drop dispense, spin-coating, dip coating, chemical vapor deposition (CVD), physical vapor deposition (PVD), thin film deposition, thick film deposition, or the like. Patterned layer 92, with features 94, may be formed from a polymerizable material such as MonoMat®, available from Molecular Imprints, Inc.

Functional materials 86a', 86b', and 86c' used to form functional layers 86a, 86b, and 86c, respectively, may each include one or more active ingredients and a binder material. The binder material may include, for example, polyethylene glycol diacrylate (PEGDA) or polyethylene glycol dimethacrylate (PEGDMA), a photoinitiator, and a solvent (e.g., water). The active ingredient(s) and binder material for each layer may be mixed together to form a liquid with a viscosity suitable for the selected method of application. For example, an active ingredient and a binder may be mixed together to form a liquid with a viscosity suitable for inkjet printing (e.g., hundreds of centipoise or less).

To form functional layer 86a, functional material 86a' is disposed on removable layer 84, and the functional material is solidified. Solidification may include, for example, contact of discrete portions of the functional material 86a' with a substantially planar (e.g., blank) template to form a substantially continuous layer of the functional material between the removable layer 84 and the template. After formation of a substantially continuous layer of functional material 86a', the functional material may be solidified (e.g., polymerized) through photo exposure to form solidified functional layer 86a between removable layer 84 and the template. After solidification of the functional material 86a', the template may be separated from solidified functional layer 86a. Separation of the template from the functional layer 86a may be facilitated by pre-treatment of the template to include a release agent (e.g., a fluorinated material or a low friction material such as diamond-like carbon (DLC)) to enhance release performance. In some cases, a template may be formed of materials with inherent release properties, such as polydimethylsiloxane (PDMS) or fluorinated polyether elastomer.

Functional material 86b' may be disposed and solidified on functional layer 86a in a process similar to that described for the formation of functional layer 86a on removable layer 84. Adhesion of functional layer 86b to functional layer 86a may be achieved through bonding of exposed functional groups (e.g., acrylate or methacrylate groups) at the surface of functional layer 86a with functional groups in functional material 86b', respectively, during solidification (e.g., polymerization) of functional material 86b' to form solidified functional layer 86b. The bonding may be, for example, covalent bonding. Similarly, functional material 86c' may be disposed and solidified on functional layer 86b in a process similar to that described for the formation of functional layer 86a on removable layer 84. Adhesion of functional layer 86c to functional layer 86b may be achieved through bonding of exposed functional groups (e.g., acrylate or methacrylate groups) at the surface of functional layer 86b with functional groups in functional material 86c', respectively, during solidification (e.g., polymerization) of functional material 86c' to form solidified functional layer 86c.

Removable layer 88, which may have properties similar or dissimilar to those of removable layer 84 as further detailed herein, may be formed on solidified functional layer 86c. Formation of removable layer 88 may be similar to that described herein for removable layer 84. For example, removable layer 88 may be applied to functional layer 86c in a process including drop dispense, spin-coating, dip coating, chemical vapor deposition (CVD), physical vapor deposition (PVD), thin film deposition, thick film deposition, or the like. In some cases, removable layers 84 and 88 have substantially the same composition. In other cases, removable layers 84 and 88 may have different compositions. Removable layers 84 and 88 are selected to be non-toxic, biocompatible, and inert with respect the binders and active ingredients in functional layers 86a-86c. Removable layers 84 and 88 may include, for example, PMMA, PVA, or gelatin.

In some cases, adhesion layer 90 is optionally formed on removable layer 88. Adhesion layer 90 may be formed of a composition described in U.S. Pat. No. 7,759,407, which is hereby incorporated by reference herein in its entirety. During processing of patterned layer 92, adhesion layer 90 may help minimize separation distortion by adhering patterned layer 92 to multilayer substrate 58 during separation of imprint template from patterned layer 92a. Patterned layer 92 may be formed on adhesion layer 90 or removable layer 88 with a patterned template in a process similar to that described above with respect to FIGS. 1 and 2. Patterned layer 92 may be formed, for example, from MonoMat®. Patterned layer 92 may be a pillar tone or hole tone layer. In some cases, a hole tone layer may be advantageous. Features 94 of patterned layer 92 have a dimension less than about 100 nm. For example, a diameter of holes in a hole tone layer may be about 100 nm or less, or about 50 nm or less.

Figure 5B:
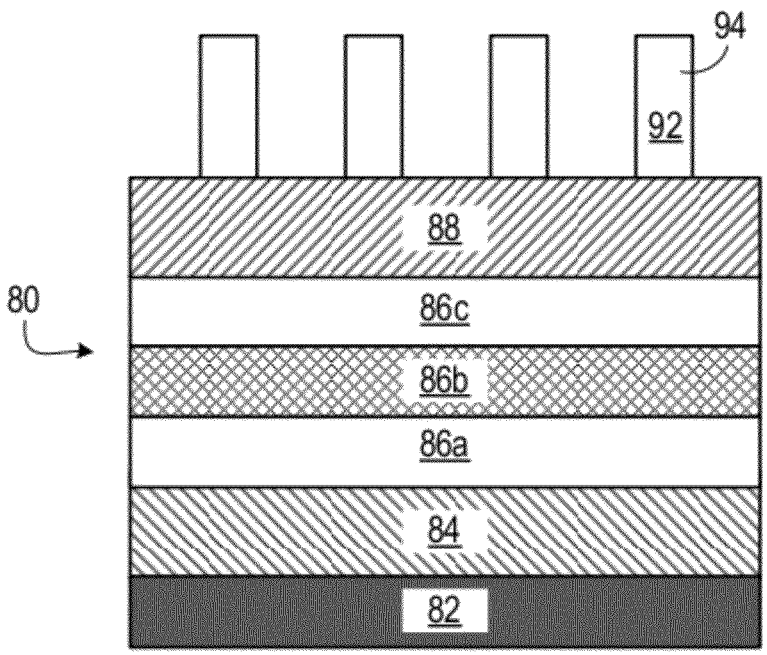

Following the process described with respect to the formation of the multilayer substrate and patterned layer of FIG. 5A, a de-scum etch (e.g., with $O_2$) can be performed to remove the residual portion of patterned layer 92 and underlying portions of adhesive layer 90, if present. As shown in FIG. 5B, the de-scum etch leaves features 94 of patterned layer 92 exposed above removable layer 88. With features 94 as a guide, a process such as VUV/$O_3$, oxygen ashing, reactive ion etching, or argon ion etching may be used to etch through patterned layer 92 into the multilayer substrate 80.

In patterned layer 92, polymer bond energies may be between about 2 and about 5 eV. Ions gaining between about 20 and about 2000 eV have the ability to alter the polymer surface of patterned layer 92. See, for example, Egitto, *Plasma Etching and Modification of Organic Polymers*, Pure and Applied Chemistry, 62:9 (1990) 1699-1708; Kushida et al., *Dry-Etching Durability of Copolymers and Polymer Blends of Vinylnaphthalene or α-Methylstyrene with Methyl Methacrylate*, Japanese Journal of Applied Physics, 34:1:8A (1995) 4234-4238; and Cho et al., *Identification of Hydrophilic Group Formation on Polymer Surface during $Ar^+$ Ion Irradiation in $O_2$ Environment*, Material Research Society Symposium Proceedings 438 (1997) 517-532, all of which are hereby incorporated by reference herein in their entirety.

An inert gas, such as argon gas, can be used for dry etching of patterned layer 92 in a sputtering process referred to as ion milling or etching. The use of an inert gas may beneficial in avoiding unwanted reactions with functional materials in the functional layers. The energy given to the $Ar^+$ ions can be controlled by controlling the RF bias given to the substrate. Argon can be used as an etchant through two physical etch processes—argon sputter etching (SE) and argon ion beam etching (IBE). See Koh et al., *Surface Modification of Polymer by Ion Assisted Reaction in Reactive Gases Environment*, Material Research Society Symposium Proceedings 438 (1997) 505-510, which is hereby incorporated by reference herein in its entirety.

A high degree of physical etching yields good anisotropy. Selectivity can be attained by introducing gases like $CHF_3$, $O_2$, etc. along with Ar to get a physical and chemical etch combination. A pure physical etch process may be slower than a combined physical and chemical etch process. To increase etch rates, the energy given to the ions may be increased. Sputter depth profiling shows that sputter etching with $Ar^+$ ions at 5 keV penetrates several nanometers below the polymer surface. This energy is enough to create homolytic scission of a large number of C—C and/or C—H bonds forming two radicals with each scission and undergoing subsequent reactions. See Hollander et al., *On Depth Profiling of Polymers by Argon Ion Sputtering*, Plasma Processes and Polymers, 4 (2007) 773-776, which is hereby incorporated by reference herein in its entirety.

The homolytic scission may change the composition of patterned layer 92 if it is sputtered with $Ar^+$ ions at high energy for a long duration. However, the energy, quantity and time of $Ar^+$ ions in the plasma can be controlled to achieve desired results. For example, it has been shown that $Ar^+$ ions with energy of 1 keV did not have significant effect in changing in surface chemistry (one measure being the contact angle of water on the surface which indicates presence of C=O, (C=O)—O, C—O and other hydrophilic groups). Thus, argon ion etching may be used to etch a sacrificial patterned layer without adversely affecting (e.g., without reacting with) layers in a multilayer substrate. This advantage of argon ion etching may be significant, since other etching processes may interact adversely (e.g., chemically) with functional layers in the multilayer substrate, for example, altering a pharmaceutical composition to decrease efficacy.

Figure 5C:
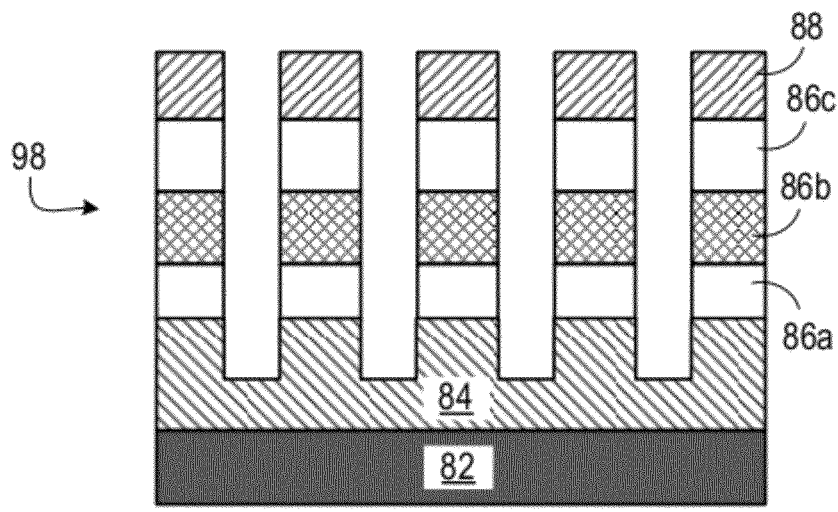
Figure 5D:
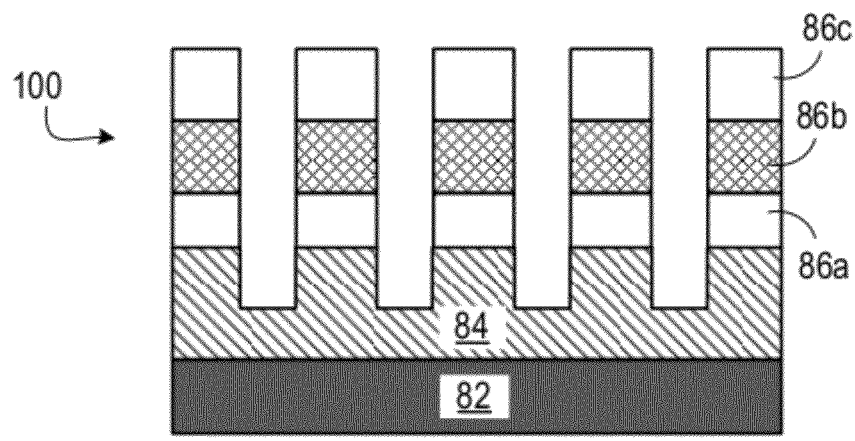

As shown in FIG. 5C, a pattern of the patterned layer may be transferred through multilayer substrate into removable layer 84 to form patterned structure 98. After the pattern is transferred into the multilayer substrate 80, a lift-off or release process can be used to form multilayer nanoparticles with functional layers 86a-86c. In some cases, the lift-off process is a one-step process with a single solvent. In other cases, the lift-off process is a two-step process with two different solvents. For example, if removable layers 84 and 88 have different solubilities, removable layer 88 can be dissolved (e.g., by dipping patterned structure 98 in a first solvent) to yield patterned substrate 100. As shown in FIG. 5D, after removable layer 88 has been removed, functional layers 86a-86c remain adhered to removable layer 84.

Patterned structure 100 may be further processed to separate multilayer nanoparticles from removable layer 84 and substrate 82. For example, the multilayer structure 100 may be further processed, or a second solvent can be used to lift off or dissolve removable layer 84. After removable layer 84 has been lifted off or dissolved, multilayer nanoparticles 102 with functional layers 86a-86c, shown in FIG. 5E, may be collected from the second solvent and processed further (e.g., dried). In some cases, a single solvent may be used to dissolve removable layers 84 and 88, such that multilayer nanoparticles 102 are formed directly from patterned structure 98 without forming patterned structure 100

Solvents used to dissolve removable layers 84 and 88 are preferably non-toxic, biocompatible, and inert with respect the binders and active ingredients in functional layers 86a-86c. Solvents that may be used include, for example, water, acetone and/or DMSO. For example, water can be used as a solvent for a removable layers including, for example PVA or gelatin. Acetone can be used as a solvent for a removable layer including PMMA. Removable layer and solvent combinations can be be selected to achieve selective dissolution of the removable layers. For example, two removable layers can be formed of PVA and PMMA, respectively. DMSO or water can be used to dissolve the PVA layer, but DMSO or water do not dissolve PMMA. Subsequent treatment with e.g. acetone can then dissolve the PMMA layer. Similarly, the two removable layers can be formed of PVA and PAA, respectively. Again DMSO can be used to dissolve the PVA layer, but DMSO does not dissolve PAA. Subsequent treatment with water can then dissolve the PAA layer. In some cases, dilute HF is used to dissolve silica-containing layers. Silica-containing layers can be used, for example, as temporary masking layers when a substrate is exposed to an oxygen plasma etch.

In some cases, after removable layer 88 is removed and before removable layer 84 is removed, patterned substrate 100 may be dried. Drying may include, for example, drying at room temperature in an inert atmosphere (e.g., $N_2$) for about an hour or more (e.g., up to 24 hours, up to 72 hours, or longer). Drying patterned substrate 100 before releasing the multilayer nanoparticles from substrate can be advantageous in post-processing of the resulting multilayer nanoparticles in processes including surface loading of the drug with enzymes, with an additional drug, or the like or surface charging one or more layers of the multilayer nanoparticles (e.g., surface charging a drug-loaded layer). This drying step provides flexibility to tailor the multilayer nanoparticle or nanoparticle drug carrier further to suit in-vitro testing or in-vivo testing and delivery requirements.

In combination with the above, or as separate processes, resulting nanoparticle surfaces can be further modified prior to release from the substrate. For example, the surface of a nanoparticle can be functionalized with a different functional group (—COO— to —NH2+) to attach subsequent functional molecules (ligands) at these sites, which can, for example, enhances the internalization of such nanoparticles by targeted cells. This may be accomplished by incubation, either in solution or through vapor deposition, with molecules having reactive groups on one end specific for the available functional group of the functional layer polymer(s) and with the other end having the desired functional group. With such approach reactive carboxylic groups on the surface of nanoparticle can, for example, essentially be replaced with reactive amine groups or vice versa. As another example, nanoparticles can be exposed to ammonia (NH3) plasma to functionalize the surface of nanoparticles. Resultant nanoparticles can also be incubated with drug loaded solvent, again either through solution or through vapor deposition, where the drug is absorbed onto on the surface of the nanoparticle after a period of exposure. The surface charge of the nanoparticle can also be modified, i.e., from negative to positive or vice versa, or from a low negative or positive to a high negative or positive, or vice versa. Such charge modification may improve dispersion stability of the nanoparticle in liquid media, and may play a role in uptake by targeted cells for medial drug delivery and diagnostics. For example, adsorption of cationic (Polyethyleneimine, PEI) and anionic (Polyacrlyic acid) polymeric surfactants can modify the surface charge of the resultant nanoparticles through exposure to such surfactants either in solution or vapor form. Surface modification can also include increasing hydrophillicity or hydrophobicity of the nanoparticle surface. For example, an increase in hydrophobicity may increase the ability of the nanoparticle embed and stick to the hydrophobic layer of the bi-lipid cell membrane of animal cells, increasing the chances the cell will internalization of the nanoparticle. Hydrophobicity and hydrophilicity can be modified e.g., through surface energy modification of polymers using different gas plasma in an RIE etch process. For example by using a fluorine gas plasma ($CF_4$, $CHF_3$, $SF_6$) a polymer surface can be made less hydrophilic compared to if it were etched in an oxygen gas plasma (He, Ar, $NH_3$, $O_2$). In an example, removable layer 84 includes PMMA (which dissolves in acetone) and removable layer 88 (under the masking layer if present) is PVA (soluble in water). Functional layers 86a-86c are different PEGDA mesh layers, and can independently be drug-loaded or non-drug loaded. After water is used to dissolve removable layer 88, patterned substrate 100 remains. Patterned substrate 100 is then exposed to an aqueous solution of polyethyleneimine (PEI, which is cationic and dissolves in water) for a sufficient time to allow at least the negatively charged PEGDA functional layers 86a-86b to become positively charged. Patterned substrate 100 is then dried, and the positively charged multilayer nanoparticles 102 are harvested by dissolving removable layer 84 with acetone. Alternatively, negatively charged multilayer nanoparticles 102 can be formed in a similar process with different reagents. Charged multilayer nanoparticles are useful for in-vitro and in-vivo studies. For example, for in-vitro studies, cells have a higher affinity for positively charged nanoparticles than negatively charged nanoparticles since cell membranes are negatively charged and have low affinity for internalizing negatively charged particles.

Figure 6A:
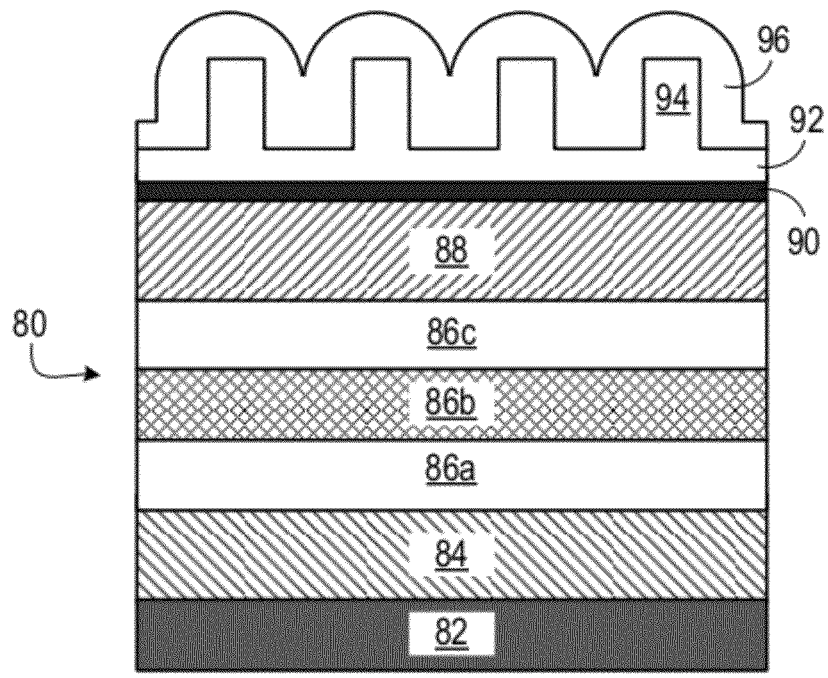
FIGS. 6A-6E illustrate simplified side views of formation of multilayer nanoparticles by imprint lithography.

In some cases, a hard mask layer may be used in a nanoimprint lithography process to form multilayer nanoparticles. FIG. 6A illustrates multilayer substrate 80 formed as described with respect to FIG. 5A, with hard mask layer 96 formed on patterned layer 92 by methods known in the art with, for example, a silicon-containing material. Hard mask layer 96 may be deposited on patterned layer 92 through a process such as spin-coating, CVD, PECVD, imprinting methods, and the like.

Figure 6B:
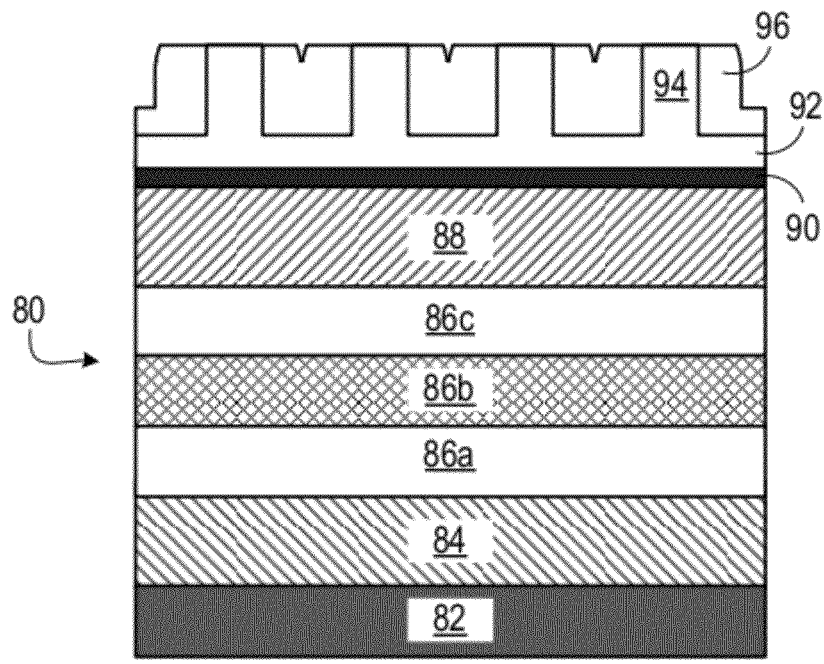
Figure 6C:
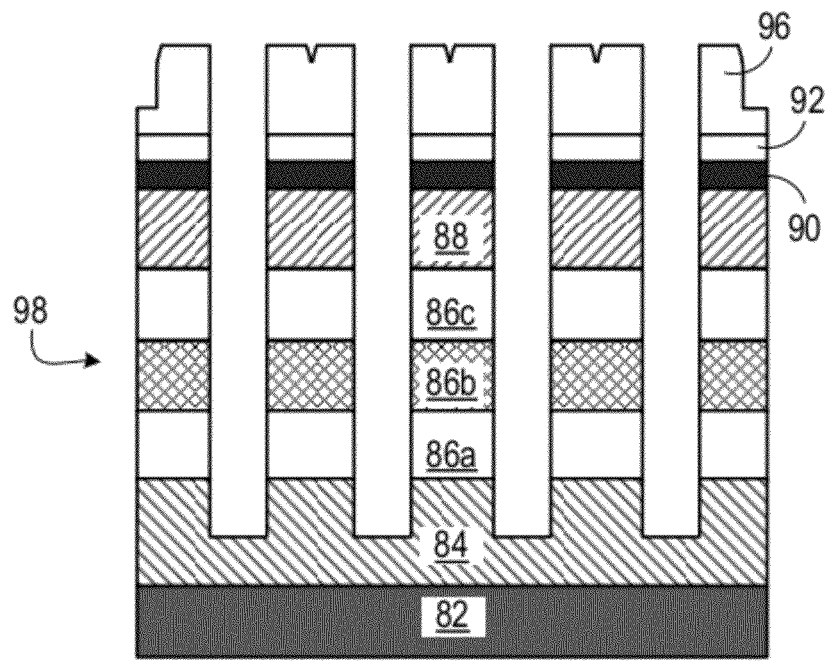

Following the process described with respect to the formation of the multilayer substrate 80, patterned layer 92, and hard mask layer 96, a sputter or dry etch method may be used to remove at least a portion of the hard mask layer 96, exposing portions (e.g. features 94) of the patterned layer 92, as shown in FIG. 6B. Following exposure of features 94, a process such as $VUV/O_3$, oxygen ashing, reactive ion etching, or argon etching may be used to etch through the multilayer substrate 80 to removable layer 84 to form patterned structure 100, as shown in FIG. 6C.

Figure 5E:
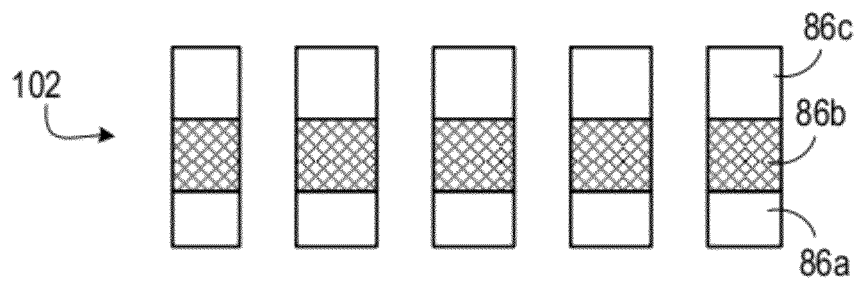

After the pattern is transferred into the multilayer substrate 80, a one- or two-step lift-off process similar to that described with respect to FIGS. 5C-5E can be used to form multilayer nanoparticles 102 with functional layers 86a-86c. In some cases, patterned structure 100, shown in FIG. 6D, may be formed in a two-step lift-off process to form multilayer nanoparticles 102 shown in FIG. 6E. For a one-step lift-off process, multilayer nanoparticles 102 may be formed directly from patterned structure 98 shown in FIG. 6C.

Figure 7A:
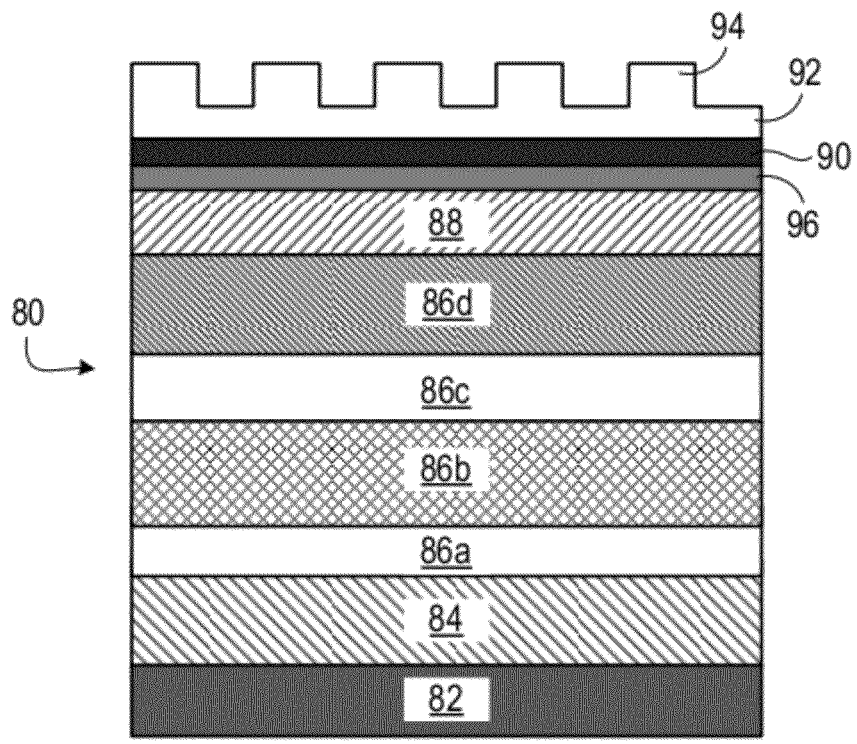
FIGS. 7A-7E illustrate simplified side views of formation of multilayer nanoparticles by imprint lithography.
Figure 7B:
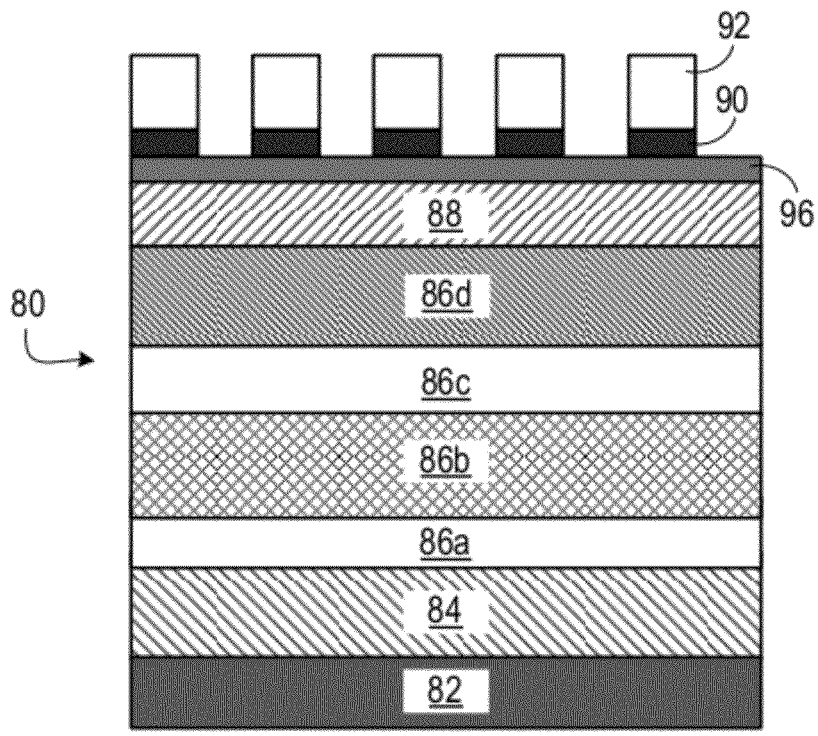
Figure 7C:
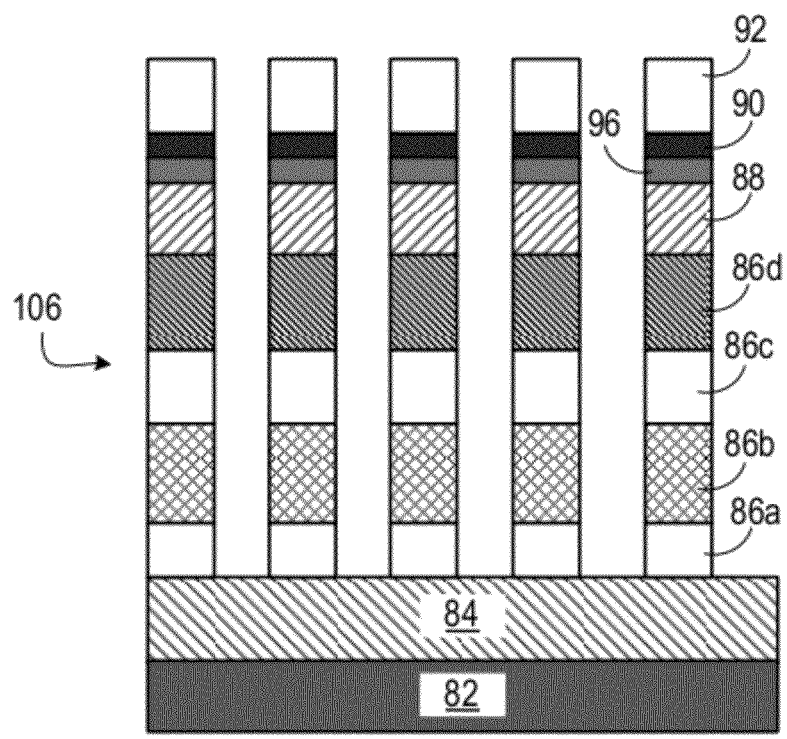
Figure 7D:
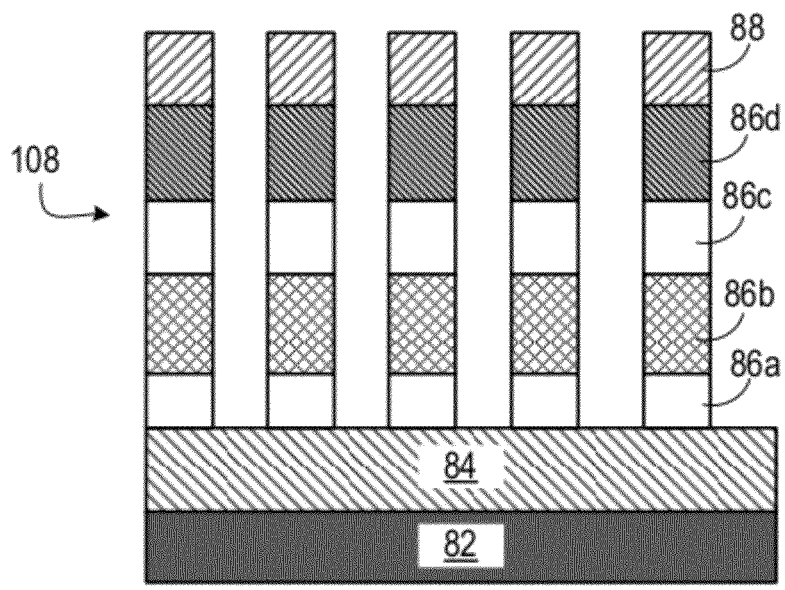

FIG. 7A illustrates a multilayer substrate 104 having base layer 82, removable layer 84, four functional layers 86a-86d, and removable layer 88. Each functional layer 86a-86d can be formed from a pharmaceutical composition including a binder and one or more active ingredients. Hard mask layer 96 is adjacent to removable layer 88. Adhesion layer 90 is adjacent to hard mask layer 96. Patterned layer 92 is formed on adhesion layer 90 with a hole tone template. Multilayer substrate 104 may be formed in a process similar to that described for multilayer substrate 80 with respect to FIG. 5A. In an example, base layer 82 is silicon, removable layer 84 is PVA, removable layer 88 is PVA, hard mask layer 96 is silicon oxide ($SiO_x$), adhesion layer 90 is ValMat® (available from Molecular Imprints, Inc.), and patterned layer 92 is PEGDA.

Figure 6D:
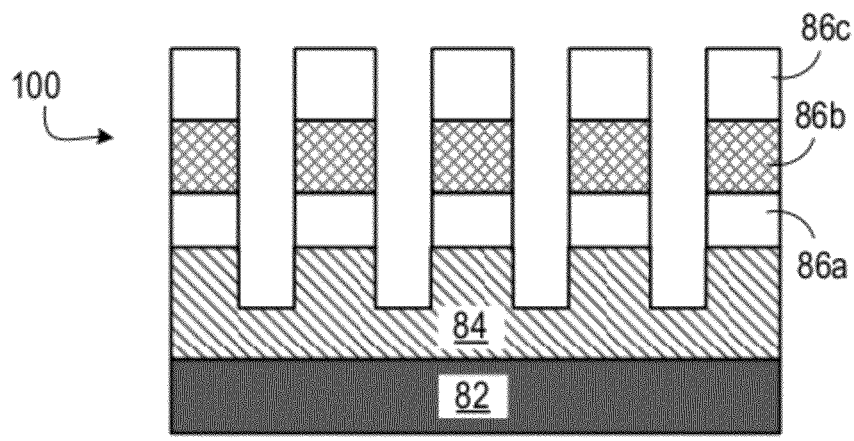
Figure 6E:
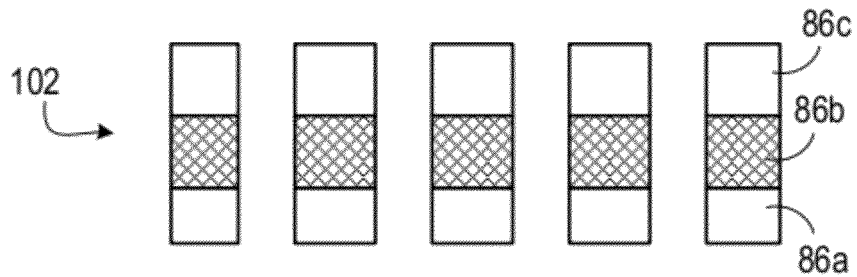
Figure 7E:
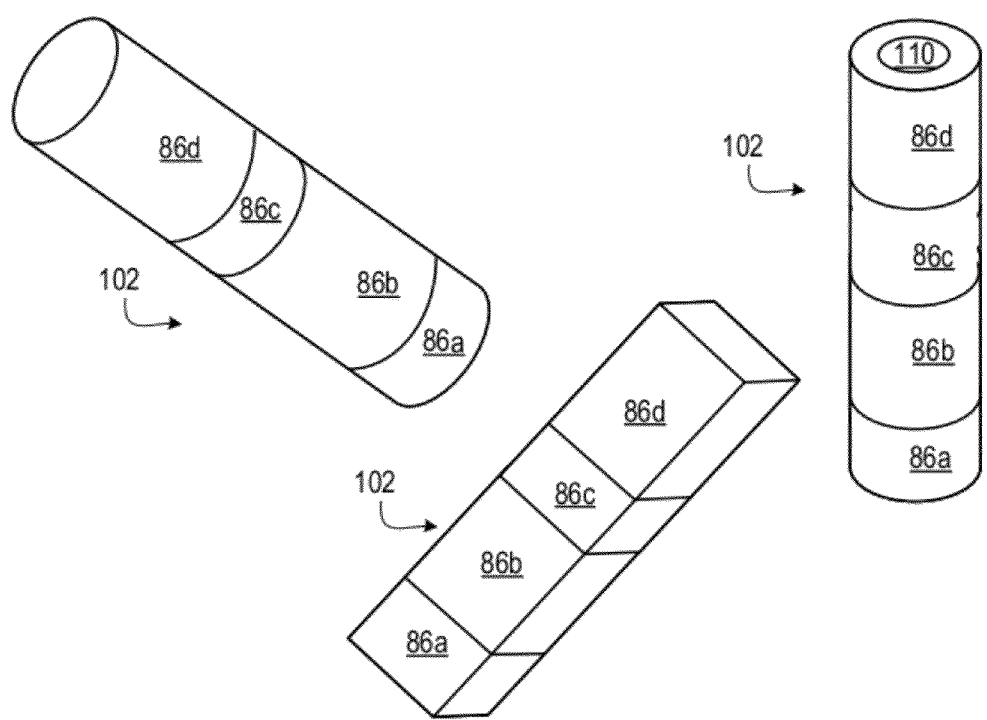

Multilayer substrate 104 may be processed to form multilayer nanoparticles suitable, for example, as controlled release medications. Processing of multilayer substrate 104 is illustrated in FIGS. 6B-6D. Referring to FIG. 6B, a portion (e.g., the residual portion) of patterned layer 92 is etched to expose hard mask layer 96 between features 94 of the patterned layer. With portions of hard mask layer 96 exposed, multilayer substrate 104 may undergo additional processing to expose portions of removable layer 84. The additional processing may include an etching step (e.g., dry etching) to yield patterned structure 106, as shown in FIG. 6C. The pillars in patterned structure 106 may be etched down to removable layer 88 to yield patterned structure 108, shown in FIG. 6D. A thickness of removable layer 88 can be selected such that hard mask layer 96 may be over-etched to ensure substantially complete removal of the hard mask layer, thus removing a portion of the removable layer 88, and allowing some of the removable layer to remain on patterned structure 108. Patterned structure 108 may be subjected to a lift-off or release process in which removable layers 84 and 88 are dissolved to yield multilayer nanoparticles 102, as shown in FIG. 7E. In an example, a lift-off process includes immersing the patterned structure 108 in a solvent (e.g., water) to dissolve removable layers 84 and 88, and collecting nanoparticles 102 from the solvent.

FIG. 7E shows a variety of multilayer nanoparticles 102 that may be formed by the process described with respect to FIGS. 7A-7D. The multilayer nanoparticles 102 may be, for example, substantially cylindrical or rectangular, or may have an irregular shape. In some cases, a template used to form a patterned layer on a multilayer substrate may be configured to form hollow pillars rather than solid pillars. That is, a recess in a template may include a protrusion (e.g., a cylindrical glass rod) such that patterned structures formed in an imprint lithography process include hollow multilayer protrusions that undergo a lift-off process to form multilayer nanoparticles 102 with openings 110. In an example, a multilayer nanoparticle 102 with opening 110 may have an outer diameter on the order of 200 nm and an inner diameter on the order of 100 nm. Opening 110 provides additional surface area for more rapid release of functional materials from the multilayer nanoparticle 102.

Figure 8:
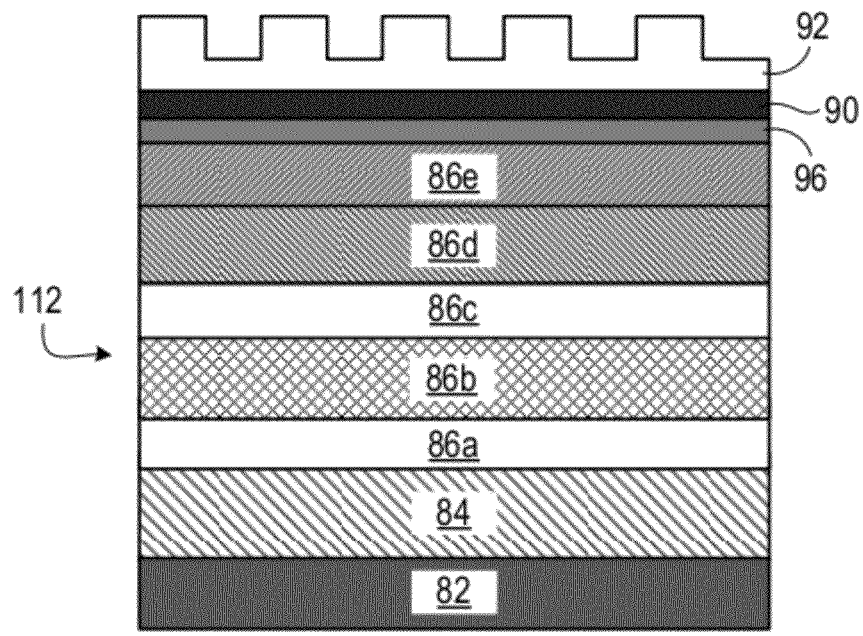
FIG. 8 illustrates a multilayer substrate formed by imprint lithography.

FIG. 8 illustrates a multilayer substrate 112 having base layer 82, removable layer 84, and five functional layers 86a-86e. Each functional layer 86a-86e can be formed from a functional material such as a pharmaceutical composition including a binder and one or more active ingredients (e.g., drugs). Hard mask layer 96 is adjacent to functional layer 86e. Adhesion layer 90 is adjacent to hard mask layer 96. Patterned layer 92 is formed on adhesion layer 90 with a hole tone template. Multilayer substrate 112 may be formed in a process similar to that described for multilayer substrate 80 with respect to FIG. 5A. In an example, base layer 82 is silicon, removable layer 84 is PVA, hard mask layer 96 is silicon oxide ($SiO_x$), adhesion layer 90 is ValMat® (available from Molecular Imprints, Inc.), and patterned layer 92 is PEGDA.

Multilayer substrate 112 may be processed to form multilayer nanoparticles. Processing may include, for example, dry etching to remove the hard mask layer, while leaving functional layer 86e intact, followed by a lift-off or release process to dissolve the removable layer 84. After removable layer 84 is dissolved, nanoparticles 102 may be collected.

Figure 9:
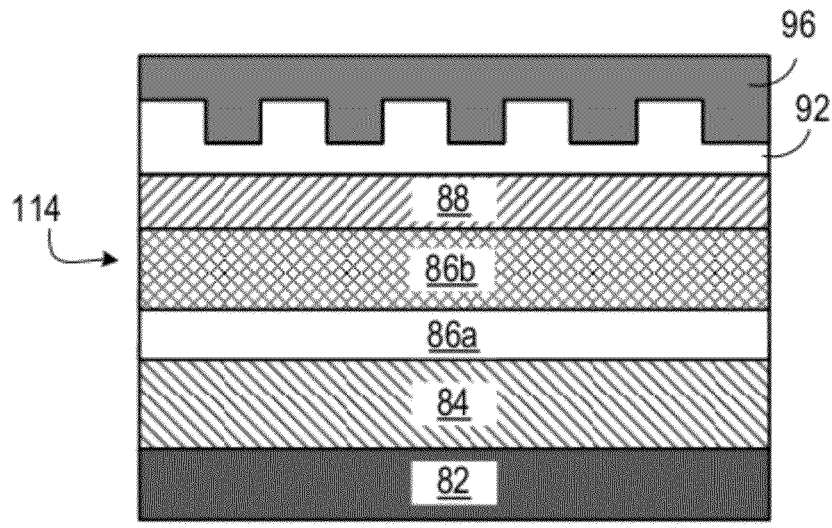
FIG. 9 illustrates a multilayer substrate formed by imprint lithography.

FIG. 9 illustrates a multilayer substrate 114 having base layer 82, removable layer 84, functional layers 86a and 86b, and removable layer 88. Patterned layer 92 is formed on removable layer 88, and hard mask layer 96 is formed on removable layer 88. One or more of the functional layers can be formed from a pharmaceutical composition including a binder and one or more active ingredients. Patterned layer 92 is formed on adhesion layer 90 with a pillar tone template. Multilayer substrate 114 may be formed in a process similar to that described for multilayer substrate 80 with respect to FIG. 5A. In an example, base layer 82 is silicon, removable layer 84 is PVA, removable layer 88 is PVA, patterned layer 92 is PEGDA, and hard mask layer 96 is silicon oxide ($SiO_x$).

Multilayer nanoparticles 102 may be formed from multilayer substrate 114 in a process similar to that described with respect to FIG. 10B. For example, portions of the hard mask layer may be etched away to expose features of the patterned layer, and the multilayer substrate 114 may be etched down to removable layer 84 to form multilayer pillars extending from the removable layer. The remaining dry mask material (as well as a portion of removable layer 88, as described with respect to FIG. 11D) may be removed by dry etching. Removable layers 84 and 88 in multilayer substrate 106 are formed from the same material, and are thus dissolved by the same solvent. After a lift-off procedure with one solvent to release multilayer nanoparticles 102 from the base layer 82, the nanoparticles may be collected.

Figure 10:
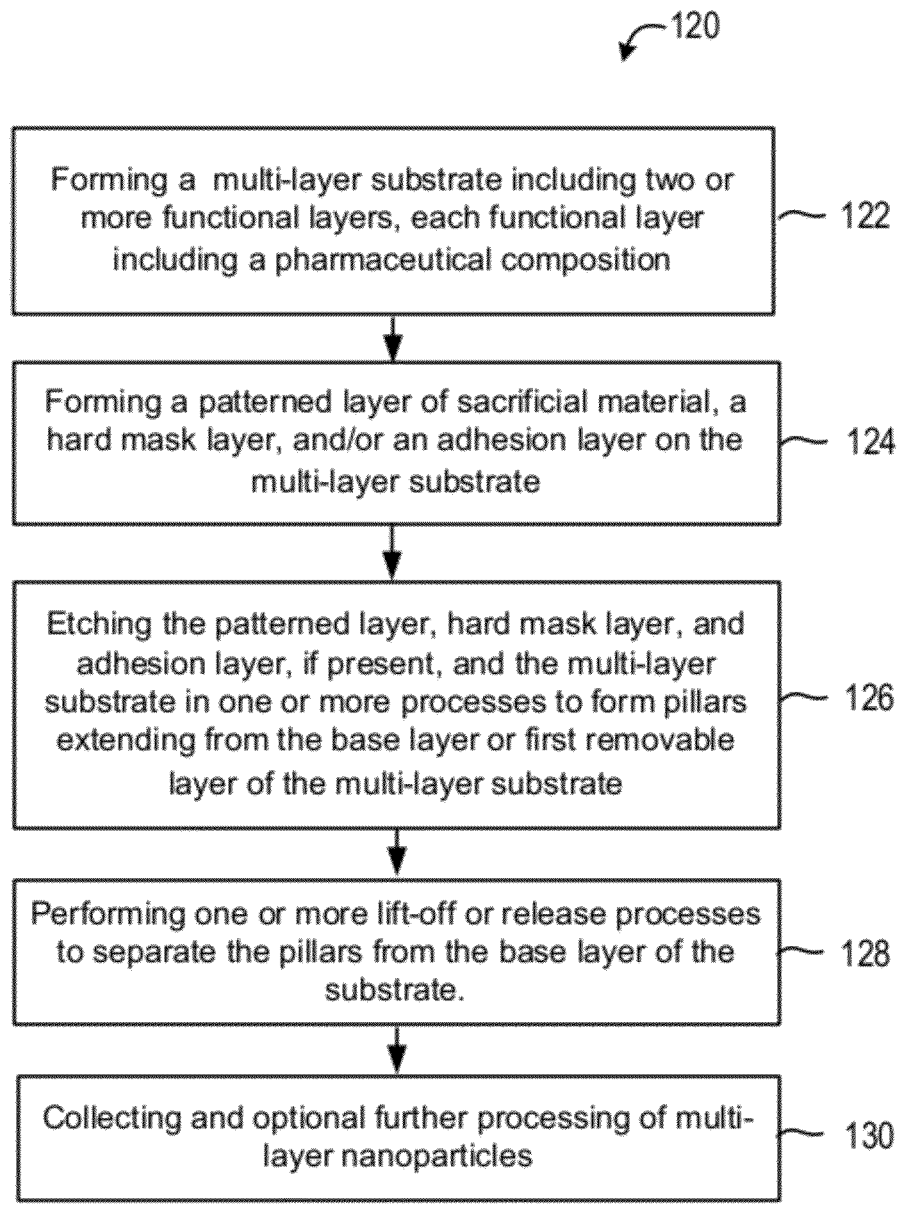
FIG. 10 illustrates a flow chart of an exemplary method of forming multilayer nanoparticles using imprint lithography.

FIG. 10 illustrates a flow chart of a method 120 of forming multilayer nanoparticles using imprint lithography. In step 122, a multilayer substrate is formed. The multilayer substrate includes a base layer, a first removable layer, two or more functional layers, a second removable layer, and an optional adhesion layer. One or more the functional layers may include a pharmaceutical composition. In step 124, a patterned layer formed of sacrificial material, a hard mask layer, an adhesion layer, or any combination thereof may be formed, in any order, on the multilayer substrate. In step 126, the patterned layer, hard mask layer, and adhesion layer, if present, and the multilayer substrate are etched in one or more processes to form pillars that extend from the base layer or first removable layer of the multilayer substrate. In step 128, one or more lift-off or release processes are performed to separate the pillars formed in step 126 from the base layer of the substrate. When the first and second removable layers are formed from the same material or from materials that have similar solubility properties, a single lift-off step is needed to release the multilayer nanoparticles from the base layer. When the first and second removable layers are formed from different materials that have different solubility properties, two lift-off steps are needed to release the multilayer nanoparticles from the base layer. In step 130, the multilayer nanoparticles are collected and subjected to further processing as desired.

There are numerous barriers to drug delivery in human beings. When a drug is delivered through the blood stream it has to overcome barriers including cells of the recticuloendothelial system (RES) (e.g., in the spleen, liver, etc.) which are a part of the immune system, renal filtration (kidney) of blood and biological membrane barriers such as the plasma membrane, the endosomal membrane and the nuclear membrane of the target cell. By creating drug delivery agents at the submicron scale, physical barriers and RES uptake can be avoided thereby allowing efficient travel and uptake of the drug loaded nanoparticles to target sites in the body. For successful drug delivery the nanoparticle drugs further need to overcome resistance at the cellular level to enter the cytoplasm of the cell and reach the ribosome and/or the cell nucleus where the drug needs to be released. The nanoparticle drug carriers are taken up by endosomes of the target cell(s) in order to transport the particles from the plasma membrane to the lysosome for digestion. Nanoparticles for drug delivery purposes need to break through the endosome membrane or the lysosome membrane to avoid being destroyed by the lysosome. Once the nanoparticles break through the endosome or lysosome membrane, they enter the cytoplasm. The nanoparticles can then target the ribosome or enter the nucleus via the nucleus membrane. To avoid membrane resistance issues, the nanoparticles loaded with drug can be engineered to be multifunctional so that it can overcome such barriers and release a drug at a pre-defined rate. Multifunctionality can be added to nanoparticle drug carriers by adding various agents in different layers of a multilayered nanoparticle drug carrier. Nanoparticles can be manufactured in a multilayered fashion for various embodiments as described below.

Figure 11:
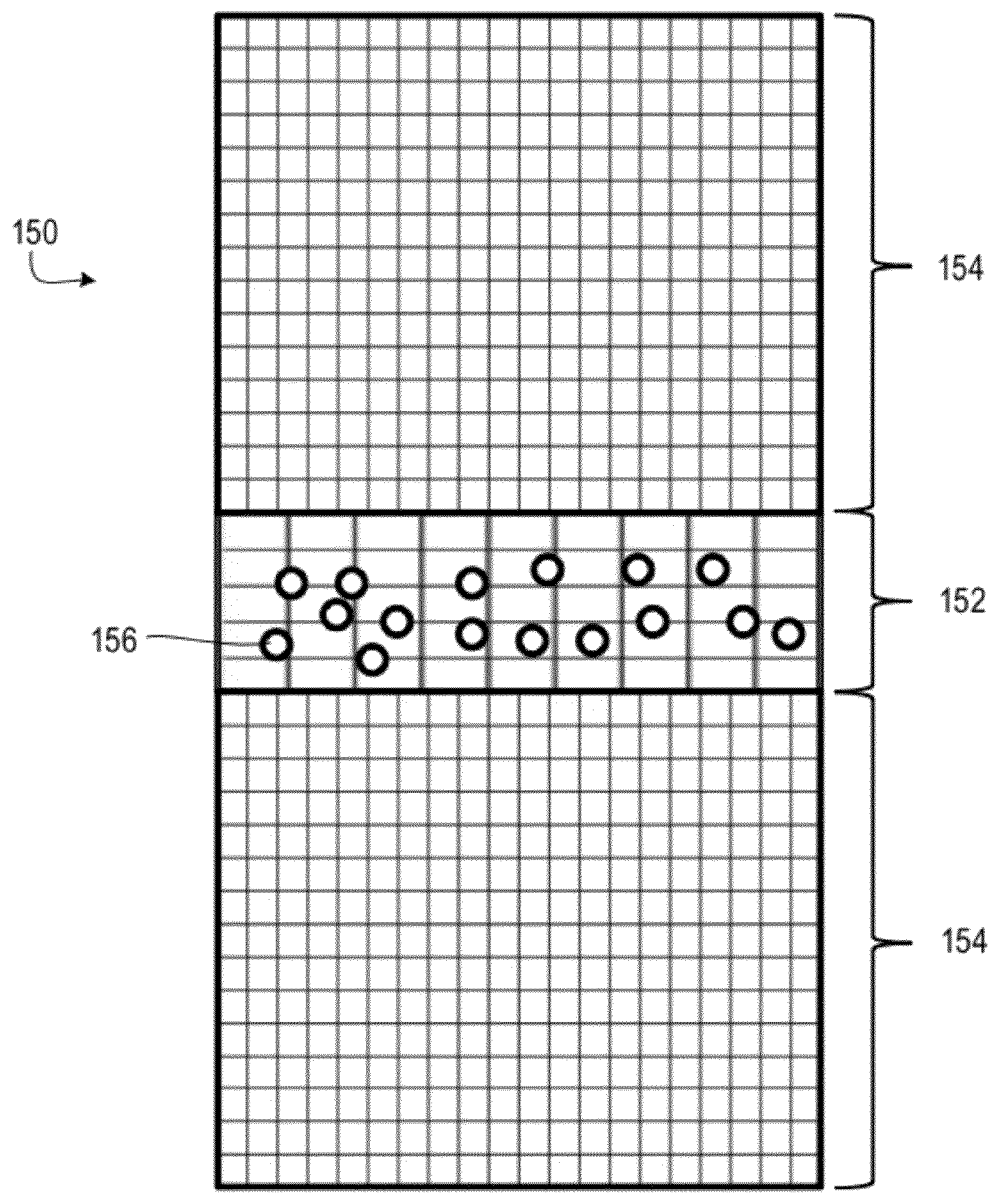
FIG. 11 is a schematic cross-sectional view of a nanoparticle drug carrier.
Figure 12:
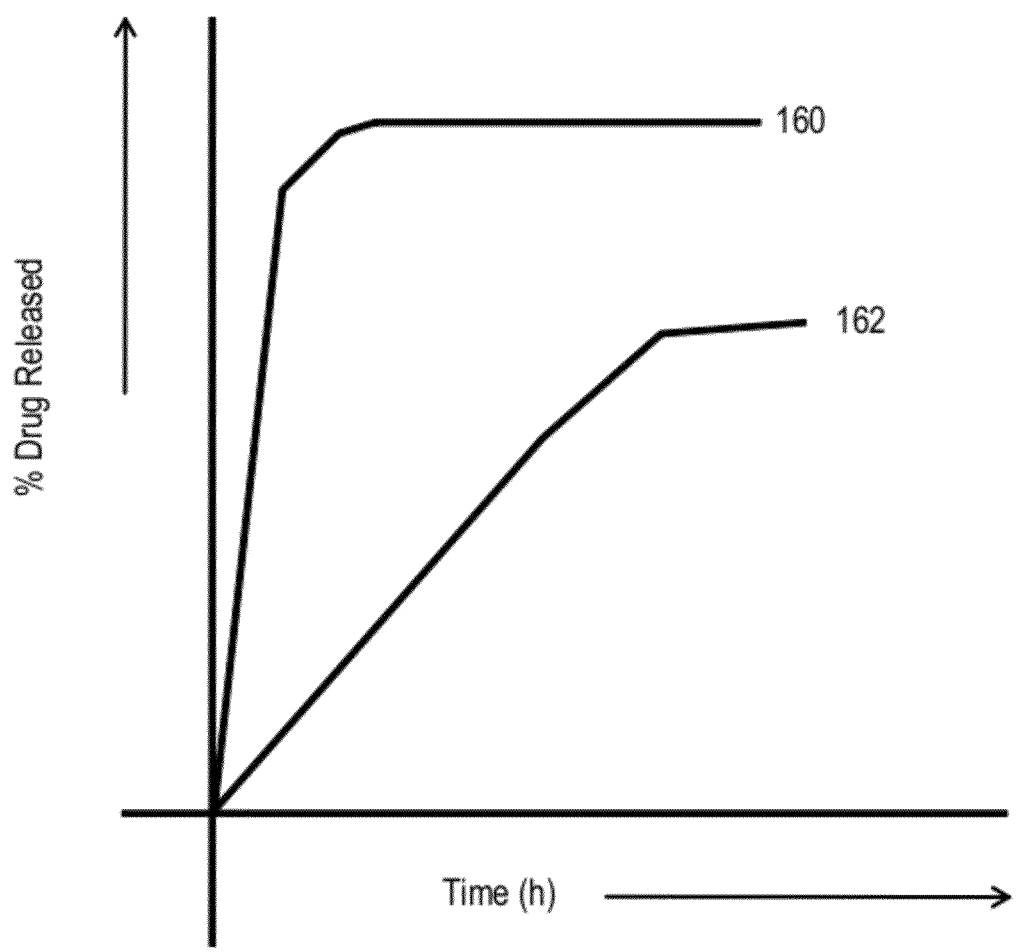
FIG. 12 is a plot showing drug release from nanoparticle drug carriers as a function of time.

For constant or zero order release kinetics, the release rate of drug agents from the nanoparticle carrier is controlled by diffusion of the drug through the carrier or degradation of the carrier structure/matrix, thereby releasing the drug. It is difficult to control drug release through degradation of carrier structures as these structures swell after being in the blood and cell medium, thereby increasing the drug diffusion out of the loose matrices. FIG. 11 shows nanoparticle carrier 150 with inner matrix 152 and outer matrices 154. Inner matrix 152 includes drug particles 156. Each of outer matrices 154 forms a tighter barrier layer matrix, compared to the structure of inner matrix 152. As used herein, a "tighter" matrix generally refers to a more closely packed polymeric matrix or mesh network. For example, a higher molecular weight polymer with a longer chain length yields a more loosely packed cross-linked structure than a lower molecular weight polymer with a shorter chain length. The presence of outer matrices 154 can curb diffusion of drug 156 from inner matrix as it degrades in the cell. The density of inner matrix 152 and outer matrices 154 can be selected to achieve a near zero order kinetic profile, thereby supplying drug particles 156 at a substantially continuous rate over time. FIG. 12 is a graph showing theoretical release kinetics (% drug released vs. time) for drug particles in a substantially homogenous nanoparticle carrier (plot 160) and a nanoparticle carrier with tighter outer matrices 154 (plot 162) as shown in FIG. 11.

Near zero-order drug release can also be achieved with a nanoparticle carrier formed by sandwiching a hydrophobic layer with embedded drug particles between two hydrophilic layers, between two hydrophobic layers, or between a hydrophilic layer and a hydrophobic layer, as described in Qui et al., *Design and Evaluation of Layered Diffusional Matrices for Zero-Order Sustained-Release*, Journal of Controlled Release, vol. 51, pp. 123-130, 1998, which is hereby incorporated by reference herein in its entirety.

Figure 13:
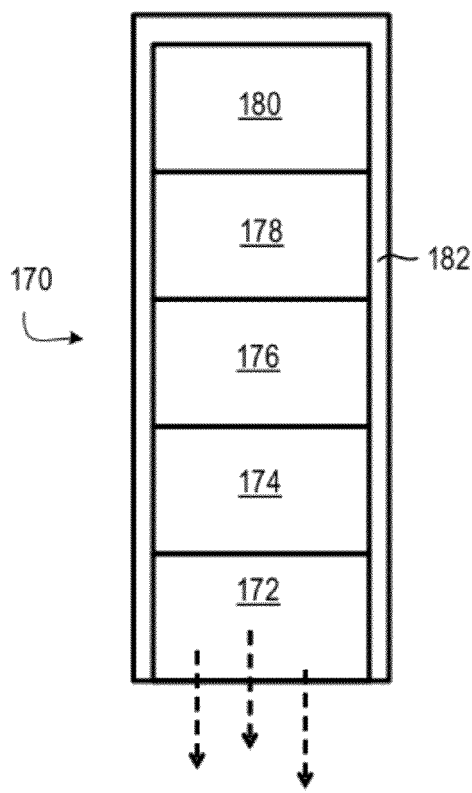
FIG. 13 is a schematic cross-sectional view of a coated nanoparticle drug carrier with barrier layers.

Nanoparticle drug carriers can be structured in way to release drug at pre-defined time (e.g., programmable release rate) or in a pulsating fashion (e.g., pulsated release kinetics). As described in Qui et al., *Design of a Core-Shelled Polymer Cylinder for Potential Programmable Drug Delivery*, International Journal of Pharmaceutics, vol. 219, pp. 151-160, 2001, which is hereby incorporated by reference herein in its entirety, such release kinetics may be favorable for treating certain types of diseases. FIG. 13 shows a cross-section of nanoparticle carrier 170 with drug-loaded layers 172, 176, and 180 and non-loaded layers 174 and 178 stacked to create a repeating unit of drug-loaded and non-loaded layers. Nanoparticle carrier 170 is partially surrounded by coating 182, such that layers 172, 174, 176, 178, and 180 are released sequentially in the direction indicated by the arrows. In some embodiments, coating 182 is formed by vapor deposition of a non-toxic hydrophobic material such as PMMA.

Figure 14:
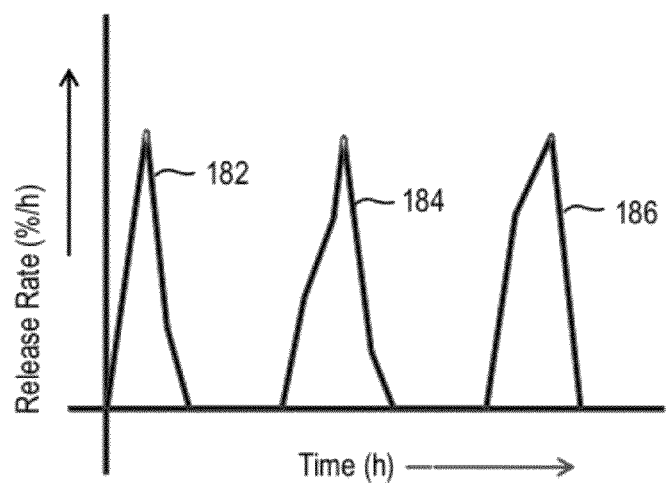
FIG. 14 is a plot of release rate over time for a multilayered nanoparticle drug carrier.
Figure 18:
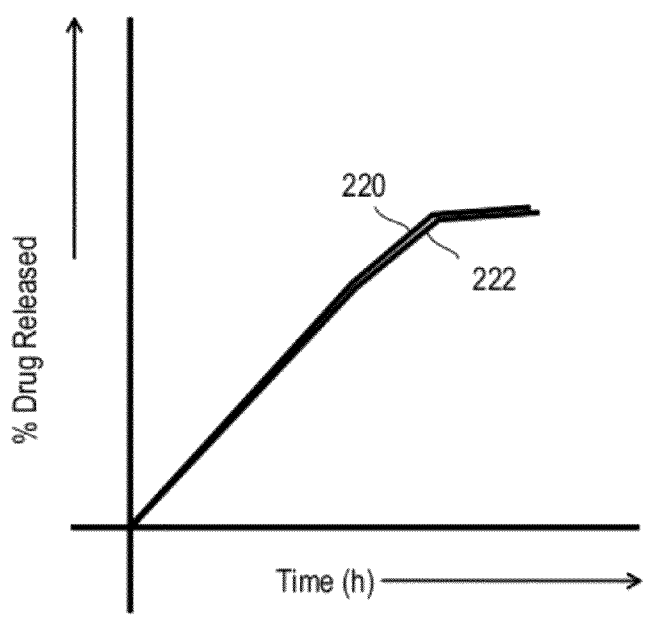
FIG. 18 is a plot showing drug released over time for nanoparticle drug carriers shown in FIG. 21.

The composition of drug-loaded layers 172, 176, and 180 and non-loaded layers 174 and 178 can be selected to yield a desired release response. For example, if drug-loaded layers 172, 176, and 180 have the same composition, the release response shown in FIG. 18 is observed, in which peaks 182, 184, and 186 correspond to the release of the same drug from layers 172, 176, and 180. In another example, if layers 172, 176, and 180 have different compositions, the release response shown in FIG. 14 is observed, in which the three peaks 182, 184, and 186 correspond to the different drugs in layers 172, 176, and 180, respectively. This configuration is suitable, for example, if the drug in layer 176 needs to be released only after the drug in layer 172 has been delivered.

In certain embodiments, the composition of each drug-loaded layer 172, 176, and 180 and non-loaded layer 174 and 178 is selected such that release of the drugs in layers 172, 176, and 180 is triggered by specific changes in parameters (e.g., temperature, pH, etc.). This can be achieved by incorporating effective triggering agents into the various layers, such that a drug is released selectively in response to a particular stimulus (e.g., the presence of an enzyme or a selected pH or temperature of the environment). In an example, release of a plasmid DNA from a nanoparticle drug carrier is triggered by the presence of an enzyme. See Glangchai et al., *Nanoimprint lithography based fabrication of shape-specific enzymatically-triggered smart nanoparticles*, Journal of Controlled Release, vol. 125 (2008), pp. 263-272.

Figure 15:
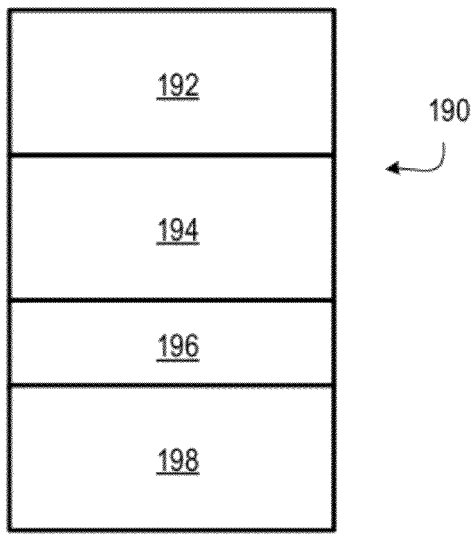
FIG. 15 is a schematic cross-sectional view of a nanoparticle drug carrier with drug-loaded layers of varying thickness.

Programmed dual drug release can be achieved using a multilayered nanoparticle carrier in which two or more drugs have different initial drug release times. The different initial drug release times can be selected based on physical shape of the nanoparticle carrier (e.g., thickness, size) and internal matrix structure (polymer chain length, molecular weight) of each layer, as described in Okuda et al., *Time-programmed Dual Release Formulation by Multilayered Drug-loaded Nanofiber Meshes*, Journal of Controlled Release, vol. 143, pp. 258-264 (2010), which is hereby incorporated by reference herein in its entirety. FIG. 15 shows a schematic cross-sectional view of a programmed dual drug release nanoparticle carrier 190, with first drug-loaded layer 192, first barrier layer 194, second drug-loaded layer 196, and second barrier layer 198. The drug in layer 192 is released first. The drug in layer 196, sandwiched between barrier layers 194 and 198, is released later.

Figure 16:
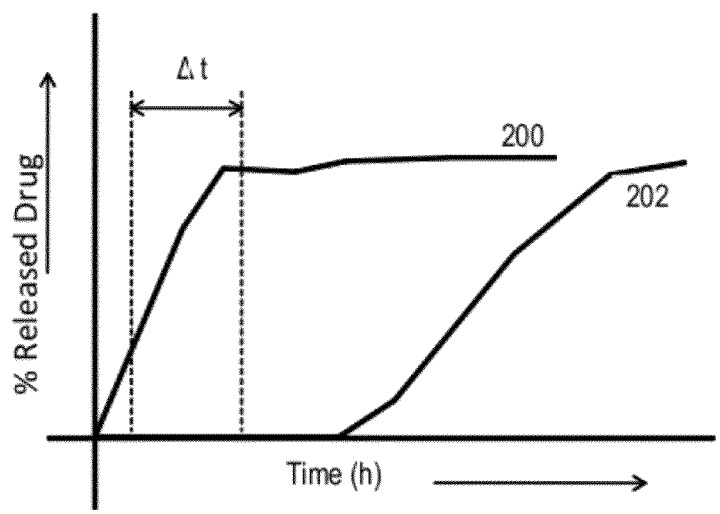
FIG. 16 is a plot showing drug released over time for a nanoparticle drug carrier shown in FIG. 19.

FIG. 16 shows a graph with plots 200 and 202 showing the release over time of the drugs in first drug-loaded layer 192 and second drug-loaded layer 196, respectively. The drug in first drug-loaded layer 192 is released first. The composition of the barrier layers 194 and 198 can be selected to achieve a desired time difference Δt between the end of the release of the drug in first drug-loaded layer 192 and the beginning of the release of the drug in the second drug-loaded layer 196.

Assuming a similar concentration of the two drugs and other factors, the difference in thickness of layers 192 and 196 may be seen along the y axis as a difference in amount of drug released. The time difference Δt can be tailored from being tens of minutes to a few hours. The structure or matrix of the barrier layers 194 and 198 can be altered (e.g., with respect to size and/or mesh density) in order to tailor the time difference Δt between drug release from layers 192 and 196.

Figure 17A:
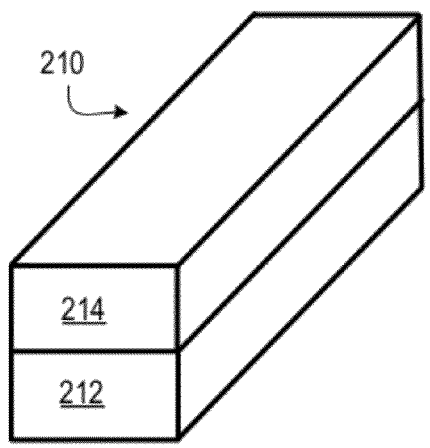
FIGS. 17A and 17B are schematic perspective views of nanoparticle drugs carrier with drug-loaded layers of similar surface area.
Figure 17B:
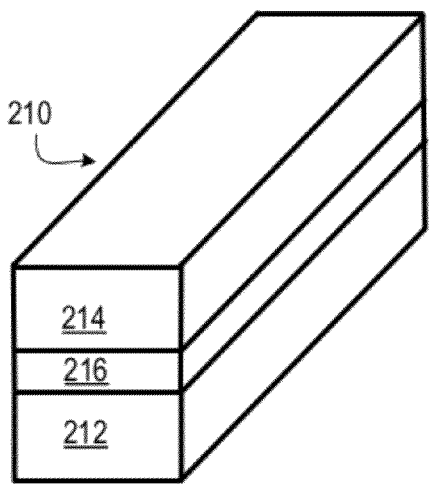

FIG. 17A shows nanoparticle drug carrier 210 with drug-loaded layers 212 and 214. FIG. 17B shows nanoparticle drug carrier 210 with drug-loaded layers 212 and 214 separated by barrier layer 216. Barrier layer 216 inhibits diffusion of a component (e.g., a drug) in layer 210 from diffusing into layer 212 and vice versa. Nanoparticle drug carriers 210 are designed such that drug-loaded layers 212 and 214 have substantially equal surface area. Since the release of a drug from a drug-loaded layer of a nanoparticle drug carrier is related to the surface area of the drug-loaded layer exposed to bodily fluids, the rate of release of drugs from layers 212 and 214 in a subject is substantially the same. FIG. 18 shows a near zero-order rate of release for drugs in nanoparticle drug carrier 210, with plots 220 and 222 showing substantially the same percent of drug release over time from drug-loaded layers 212 and 214, respectively.

Once a drug escapes the endosome or lysosome, it enters the cytoplasm. Translocation of molecules from the cytoplasm to the nucleus of the cell occurs through the nuclear pore complex (NPC). In some cases, drug permeation of the nuclear membrane can be enhanced by selecting a nanoparticle carrier with a size that allows penetration of the nuclear pores (<39 nm in diameter). In certain cases, drug permeation of the nuclear membrane can be enhanced by the addition of nuclear localization signal (NLS) peptides to the functional drug (gene carrier, DNA, etc.). This enhanced access to the nucleus can be achieved together with, or separately from, a size of the nanoparticle carrier. If the charge on the NLS peptide and the functional drug differ, however, drug delivery through the NPC may have limited success if the two oppositely charged species combine and neutralize, as described in Akita et al., *Multilayered Nanoparticles for Penetrating the Endosome and Nuclear Membrane via a Step-wise Membrane Fusion Process*, Biomaterials, vol. 30 (2009), pp. 2940-2049, which is hereby incorporated by reference herein in its entirety. With a nanoparticle carrier, a multilayered structure can be designed to separate the NLS peptide and an oppositely charged drug, thus enabling drug delivery into the nucleus of a cell with a single nanoparticle. FIG. 19A shows a schematic view of a cross-section of nanoparticle carrier 230 with drug-loaded layer 232 including drug 234, barrier layer 236, and NLS-agent-containing layer 238 including NLS agent 240. FIG. 19B shows a schematic view of a cross-section of a nanoparticle carrier 230 with drug-loaded layer 232 and NLS-agent containing layer 238. In an example, drug-loaded layer 232 includes an anionic drug (e.g., an anionic plasmid DNA) and NLS-agent-containing layer 236 includes a cationic NLS agent.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. An imprint lithography method for forming nanoparticles comprising:
    forming a multilayer substrate comprising a base layer, a first removable layer bonded to the base layer, one or more functional layers bonded to the first removable layer; and a second removable layer bonded to one of the functional layers, wherein at least one of the one or more functional layers contains a functional material;
    forming a patterned layer on a surface of the multilayer substrate in an imprint lithography process, the patterned layer comprising a multiplicity of projections and recessions;
    transferring the features of the patterned layer into the multilayer substrate in one or more etching processes to form a plurality of multilayer pillars extending from the base layer;
    dissolving the first and second removable layers with a solvent to separate pillars containing the one or more functional layers from the base layer, the separated pillars defining nanoparticles.

2. The method of claim 1 wherein the functional material is a pharmaceutical composition.

3. The method of claim 1 wherein the functional material is an imaging agent.

4. The method of claim 1 further comprising forming a hard mask layer on the patterned layer, and then etching away at least a portion of the hard mask layer before transferring the features of the patterned layer into the multilayer substrate in one or more etching processes to form a plurality of multilayer pillars extending from the base layer.

5. The method of claim 1 further comprising forming a hard mask layer over the second removable layer.

6. The method of claim 1 wherein the transferring further substantially removes the patterning layer.

7. The method of claim 1 wherein at least one of the etching processes comprises an inert gas etching process.

8. The method of claim 1 further comprising dissolving the second removable layer with a first solvent, wherein the first solvent selectively dissolves the second removable layer; and
    dissolving the first removable layer with a second solvent, wherein the second solvent selectively dissolves the first removable layer to separate the pillars from the base layer.

9. The method of claim 1 further comprising treating the surfaces of the multilayer pillars before dissolving the first removable layer.

10. The method of claim 9 wherein the surface treating further comprises coating the surface of the multilayer substrate.

11. The method of claim 9 wherein the surface treating further comprises modifying the surface of the multilayer substrate.

12. The method of claim 11 wherein the modifying is selected from the group consisting of coupling ligands or other functional molecules to the surface, modifying surface charge, and modifying the hydrophobicity or the hydrophilicity of the surface.

13. An imprint lithography method comprising:
    forming a multilayer substrate comprising a base layer, a first removable layer coupled to the base layer, one or more functional layers coupled to the first removable layer, and a second removable layer coupled to one of the functional layers, wherein at least one of the functional layers comprises contains a functional material;

forming a hard mask layer on the multilayer substrate;

forming a patterned layer over the hard mask layer in an imprint lithography process, the patterned layer comprising a multiplicity of projections and recessions;

transferring the features of the patterned layer into the hard mask and multilayer substrate in one or more etching processes to form a plurality of multilayer pillars extending from the base layer; and dissolving the first removable layer and the second removable layer with a solvent to separate the multilayer pillars from the base layer.

14. The method of claim 13 wherein the functional material is a pharmaceutical composition.

15. The method of claim 13 wherein the functional material is an imaging agent.

16. The method of claim 13 wherein the transferring further substantially removes the patterning layer and the hard mask.

17. The method of claim 13 further comprising dissolving the second removable layer with a first solvent, wherein the first solvent selectively dissolves the second removable layer; and dissolving the first removable layer with a second solvent, wherein the second solvent selectively dissolves the first removable layer to separate the pillars from the base layer.

* * * * *